US010352902B2

(12) United States Patent
Duckworth

(10) Patent No.: US 10,352,902 B2
(45) Date of Patent: Jul. 16, 2019

(54) SYSTEM, METHOD AND COMPUTER MEDIUM HAVING COMPUTER PROGRAM TO DETERMINE PRESENCE OF STRESS CORROSION CRACKING IN PIPELINES WITH PATTERN RECOGNITION

(71) Applicant: Kinder Morgan, Inc., Houston, TX (US)

(72) Inventor: Noel Duckworth, Richmond, TX (US)

(73) Assignee: Kinder Morgan, Inc., Houston, TX (US)

( * ) Notice: Subject to any disclaimer, the term of this patent is extended or adjusted under 35 U.S.C. 154(b) by 1200 days.

(21) Appl. No.: 14/039,360

(22) Filed: Sep. 27, 2013

(65) Prior Publication Data

US 2014/0088889 A1   Mar. 27, 2014

Related U.S. Application Data

(60) Provisional application No. 61/706,575, filed on Sep. 27, 2012.

(51) Int. Cl.
*G01N 27/82* (2006.01)
*G01N 27/83* (2006.01)

(52) U.S. Cl.
CPC ............ *G01N 27/82* (2013.01); *G01N 27/83* (2013.01)

(58) Field of Classification Search
CPC .................................................. G01N 27/83
See application file for complete search history.

(56) References Cited

U.S. PATENT DOCUMENTS

| | | | |
|---|---|---|---|
| 3,483,466 A | 12/1969 | Crouch et al. |
| 3,539,915 A | 11/1970 | Walters et al. |
| 3,753,085 A | 8/1973 | Morton et al. |
| 3,762,446 A | 10/1973 | Tungseth et al. |
| 4,241,430 A | 12/1980 | Kayem et al. |
| 4,507,019 A | 3/1985 | Thompson |
| 4,885,723 A | 12/1989 | Havira et al. |
| 5,182,775 A | 1/1993 | Matsui et al. |

(Continued)

OTHER PUBLICATIONS

Amineh et al. "Characterization of Surface Breaking Cracks Using One Tangential Component of Magnetic Leakage Field" IEEE Trans. Magnetics, Oct. 15, 2007, pp. 1-9.

(Continued)

*Primary Examiner* — Mohamed Charioui
*Assistant Examiner* — Brandon J Becker
(74) *Attorney, Agent, or Firm* — Bracewell LLP; Constance G. Rhebergen; Christopher L. Drymalla

(57) ABSTRACT

Embodiments of the present invention provide systems, methods, and computer medium having computer programs to determine presence of stress corrosion cracking in one or more pipelines or portions thereof such as pipeline joints by utilizing pattern recognition in pipeline data such as magnetic flux leakage data. A screening process, for example, does not affect or change how survey data is recorded such as in survey tools; only how it is analyzed after the survey data is completed. Embodiments of the systems, methods, and computer medium having computer programs can be used to screen for potential locations of stress corrosion cracking in one or more pipelines so that site excavation can occur for confirmation and validation of the output results.

70 Claims, 25 Drawing Sheets
(18 of 25 Drawing Sheet(s) Filed in Color)

(56) References Cited

U.S. PATENT DOCUMENTS

| | | |
|---|---|---|
| 5,323,429 A | 6/1994 | Roarty et al. |
| 5,479,100 A * | 12/1995 | Fowler .................. G01N 27/83 |
| | | 324/220 |
| 5,526,689 A | 6/1996 | Coulter et al. |
| 5,571,955 A | 11/1996 | Beavers et al. |
| 5,587,534 A | 12/1996 | McColskey et al. |
| 5,728,943 A | 3/1998 | Colter, Jr. et al. |
| 5,751,144 A * | 5/1998 | Weischedel ............ G01N 27/82 |
| | | 324/220 |
| 5,883,311 A | 3/1999 | Hettiarachchi et al. |
| 5,883,815 A | 3/1999 | Drakulich et al. |
| 5,943,632 A | 8/1999 | Edens et al. |
| 6,021,093 A * | 2/2000 | Birchak .................. G01V 1/44 |
| | | 181/105 |
| 6,107,811 A | 8/2000 | Caudill et al. |
| 6,155,292 A | 12/2000 | Kurata |
| 6,205,859 B1 | 3/2001 | Kwun et al. |
| 6,243,657 B1 | 6/2001 | Tuck et al. |
| 6,373,245 B1 | 4/2002 | Kwun et al. |
| 6,405,156 B1 | 6/2002 | Kern et al. |
| 6,429,650 B1 | 8/2002 | Kwun et al. |
| 6,597,997 B2 | 7/2003 | Tingley |
| 6,727,691 B2 | 4/2004 | Goldfine et al. |
| 6,995,557 B2 | 2/2006 | Goldfine et al. |
| 7,013,249 B1 * | 3/2006 | Davis ..................... G01N 17/04 |
| | | 166/250.08 |
| 7,231,331 B2 * | 6/2007 | Davis ..................... G01N 17/04 |
| | | 367/115 |
| 7,626,383 B1 | 12/2009 | Sun et al. |
| 7,899,628 B2 * | 3/2011 | Duckworth ......... G01M 5/0025 |
| | | 702/38 |
| 8,140,273 B2 | 3/2012 | Duckworth et al. |
| 9,243,972 B2 * | 1/2016 | Duckworth ......... G01M 5/0025 |
| 2001/0022514 A1 | 9/2001 | Light et al. |
| 2003/0025913 A1 | 2/2003 | Izatt et al. |
| 2003/0198374 A1 | 10/2003 | Hagene et al. |
| 2004/0076390 A1 | 4/2004 | Yang et al. |
| 2004/0095137 A1 | 5/2004 | Kwun et al. |
| 2006/0076951 A1 * | 4/2006 | Nestleroth ............ G01N 27/82 |
| | | 324/220 |
| 2007/0165234 A1 | 7/2007 | Podoleanu |
| 2007/0222436 A1 * | 9/2007 | Gao ........................ G01N 27/82 |
| | | 324/220 |
| 2007/0223643 A1 | 9/2007 | Yamane et al. |
| 2009/0234590 A1 * | 9/2009 | McNealy ............... G01N 27/82 |
| | | 702/38 |
| 2011/0062951 A1 | 3/2011 | Duckworth et al. |
| 2011/0068782 A1 | 3/2011 | Duckworth et al. |
| 2011/0098941 A1 * | 4/2011 | Duckworth ......... G01M 5/0025 |
| | | 702/38 |
| 2014/0062792 A1 | 3/2014 | Schantz et al. |
| 2014/0088889 A1 | 3/2014 | Duckworth |
| 2014/0294285 A1 | 10/2014 | Duckworth |

OTHER PUBLICATIONS

Eiber, Bob "Overview of Integrity Assessment Methods for Pipelines" Washington Cities and Counties Pipeline Safety Consortium, Nov. 2003, 20 pages.

Office Action for co-pending U.S. Appl. No. 12/950,118 dated Mar. 10, 2014.

Roberts, Brian "Monitoring the quality of welded tube and pipe" TheFabricator.com, Sep. 17, 2001, 8 pages.

M. Beller, Tools, Vendors, Services—A Review of Current In-Line Inspection Technologies, Copyright 2002, Pigging Products and Services Association, 13 pages.

Specifications and requirements for intelligent pig inspection of pipelines, Version 3.2, Jan. 2005, 30 pages.

Final Office Action for co-pending U.S. Appl. No. 12/950,118 dated Jul. 9, 2014.

Office Action for co-pending U.S. Appl. No. 12/950,118 dated Mar. 23, 2015.

Office Action for co-pending U.S. Appl.No. 12/953,720 dated Feb. 27, 2015.

Budenkov et al. "Use of Rayleigh Waves in Testing Stress-Corrosion Breaks in Pipelines by the Acoustic Emission Method" Russian Journal of Nondestructive Testing, vol. 36, No. 10, Jan. 10, 2000, pp. 763-768.

Co-pending U.S. Appl. No. 12/950,118, filed Nov. 19, 2010.

Co-pending U.S. Appl. No. 12/953,720, filed Nov. 24, 2010.

Czyz et al. "Multi-Pipeline Geographical Information System Based on High Accuracy Inertial Surveys" Proceedings of IPC 2000, International Pipeline Conference, Calgary, Oct. 2000, ASME Paper No. IPC00-138, pp. 1-5.

Evertz et al. "Test method for the investigation of the susceptibility to cracking in near neutral pH solution" Steel Research, vol. 70, No. 4+5, Apr./May 1999, pp. 183-187.

Leeds et al. "Modified analysis method helps coating fault, pipe assessment" Corrosion & Pipe Protection, vol. 83, No. 3, Mar. 2000, 11 pgs.

Leis et al. "Stress-Corrosion Cracking on Gas-Transmission Pipelines: History, Causes, and Mitigation" Proceedings, First International Business Conference on Onshore Pipelines, Berlin, Dec. 1997, 17 pgs.

Marr et al. "Procedures guide prediction, evaluation of stress corrosion" Corrosion & Pipe Protection, vol. 81, No. 3, Mar. 1998, 14 pgs.

Edwards, Graham R.; "Detection of Corrosion in Offshore Risers Using Guided Ultrasonic Waves" International Conference on Offshore Mechanics and Arctic Engineering, OMAE 2007, San Diego, CA, Jun. 10-15, 2007; pp. 1-17.

* cited by examiner

SYSTEM, METHOD AND COMPUTER MEDIUM HAVING COMPUTER PROGRAM TO DETERMINE PRESENCE OF STRESS CORROSION CRACKING IN PIPELINES WITH PATTERN RECOGNITION

RELATED APPLICATION

This application is a non-provisional of and claims the benefit of and priority to U.S. Provisional Patent Application No. 61/706,575 titled "System, Method, and Computer Medium Having Computer Program to Determine Presence of Stress Corrosion Cracking in Pipelines With Pattern Recognition" filed Sep. 27, 2012, which is incorporated herein by reference in its entirety.

BACKGROUND

Field of Invention

The present invention relates to the detection of corrosion and cracks in pipeline joints and, more particularly, to systems, methods, and computer media having computer programs which utilize pattern recognition to detect and locate stress corrosion cracking along a pipeline using transverse magnetic flux technology.

Description of Related Art

Pipelines can be prone to Stress Corrosion Cracking (SCC). At least in part because the cracks, defects or other anomalies associated with SCC can be microscopic in size, SCC is a difficult defect to detect with the current pipeline inspection tools. Special tools and technologies have been developed to assist with the detection, location and management of axial defects but SCC remains one of the most difficult features to detect and quantify.

Magnetic Flux Leakage (MFL) inspection is a robust and reliable inspection technology, which can be used effectively to detect 'crack-like' defects in the seam welds and other locations within a pipeline wall. An example of an advanced data analysis technique associated with MFL technology can be seen in U.S. Pat. Nos. 7,899,628 and 8,140,273.

Generally, MFL technology operates on the principle that where there is metal loss in the pipeline wall, a magnetic field leaks from the metal. To implement MFL inspection technology in a pipeline, an MFL tool such as an In-Line Inspection (ILI) tool is often deployed into an interior of the pipeline and is induced to travel therethrough to evaluate the pipeline wall. In some instances, the MFL tool includes magnets and brushes arranged to create a magnetic circuit with the pipeline wall and to saturate the pipeline wall with magnetic flux. A longitudinal and/or a circumferential field path is induced depending on the needs of the particular survey. Strategically placed sensors on the MFL tool can detect signals representative of the leakage of the magnetic flux from the pipeline wall at locations around a circumference of the pipeline wall over a length of the pipeline. Since anomalies such as metal loss within the pipeline wall tend to change the MFL signals detected in proportion to the size of the anomaly, the MFL signals detected from the pipeline wall can be analyzed to determine the size and location of anomalies within the pipeline wall.

Circumferential field tools offered by pipeline inspection service providers have been introduced to detect and quantify axial defects such as scrapes or gouges, seam weld conditions such as Electric Resistance Weld (ERW) anomalies, lack of fusion, and hook cracks. These tools are not generally specified as being capable of detecting tight or microscopic cracks as would be associated with SCC. ROSEN USA, one pipeline inspection service and software tool provider, identifies one of their circumferential field tools as Axial Flaw Detection (AFD), while GE-PII Pipeline Solutions, another pipeline inspection service and software tool provider, refers to theirs as Transverse Field Inspection (TFI). In addition, ultrasonic tools have been developed and introduced to detect 'crack-like' features. These ultrasonic tools are generally specified to detect SCC type cracks but experience shows that the results are inconsistent.

In normal analysis processes utilizing Transverse MFL (T-MFL) technology, detection processes have been primarily focused on the identification and quantification of volumetric metal loss anomalies along a pipeline. Patterns of data representative of the location and size of these volumetric metal loss anomalies are often displayed on one or more displays for evaluation by an analyst. Analysts have not been able use these data patterns to assess the potential for SCC at particular pipeline locations. As such, recognized by Applicant is the need for a new analysis and identification process that overcomes such limitations.

SUMMARY OF INVENTION

In view of the foregoing, embodiments of the present invention provide systems, methods, and computer media having computer programs to determine presence of SCC in one or more pipelines or portions thereof such as pipeline joints by utilizing pattern recognition in pipeline survey data such as MFL data. A screening process, for example, does not affect or change how survey data is recorded such as in survey tools; only how it is analyzed after the collection of the survey data is completed. Embodiments of the systems, methods, and computer media having computer programs can be used to screen for potential locations of SCC in one or more pipelines, and to output these potential locations so that site excavation can occur for confirmation and validation of an assessed potential for SCC at the output locations.

Embodiments of the present invention also provide systems, methods, and computer media having computer programs which utilize pattern recognition to determine presence and location of SCC along a welded or non-welded pipeline using MFL technology. For example, according to an embodiment of the present invention, a pattern recognition protocol can use Circumferential Scan (C-Scan) MFL data to locate pipe joints with an elevated potential of containing SCC.

An embodiment of a system to detect SCC associated with pipeline joints of a longitudinally extending pipeline positioned to transport fluids associated with energy therethrough, for example, can include one or more displays, one or more processors in communication with one or more pipeline inspection survey tools, and a non-transitory storage medium or media having one or more computer programs stored thereon and readable by the one or more processors. The one or more computer programs can include a set of instructions that, when executed by the one or more processors, causes the one or more processors to perform the operations of: receiving, in a first process, magnetic flux leakage data from the one or more pipeline inspection survey tools related to one or more joints of one or more longitudinal pipelines defining a pipeline joint, displaying, in a second process, the magnetic flux leakage data on the one or more displays as one or more selected patterns of data representing selected signal characteristics of the pipeline joint, analyzing, in a third process, the magnetic flux leakage data responsive to the selected signal characteristic and one or more predetermined patterns of the magnetic flux leakage data of the pipeline joint being displayed on the one or more displays, the one or more predetermined patterns of the magnetic flux leakage data being indicators of potential SCC associated with the pipeline joint, and determining, in a fourth process, a location of potential SCC associated with the pipeline joint responsive to the one or more predetermined patterns of magnetic flux leakage data being displayed on the one or more displays.

Another embodiment of a system to detect SCC associated with a pipeline, for example, can include one or more displays, one or more processors in communication with the one or more displays, and a non-transitory storage medium or media having one or more computer programs stored thereon and readable by the one or more processors. The one or more computer programs can include a set of instructions that, when executed by the one or more processors, causes the one or more processors to perform the operations of: receiving, in a first process, data associated with an inspection of one or more pipelines, displaying, in a second process, the data on the one or more displays as one or more selected patterns of data representing selected signal characteristics of the one or more pipelines, analyzing, in a third process, the data responsive to the selected signal characteristics and one or more predetermined patterns of the data of the one or more pipelines being displayed on the one or more displays, the one or more predetermined patterns being indicators of potential SCC associated with the one or more pipelines, and determining, in a fourth process, a location of potential SCC associated with the pipeline responsive to the one or more predetermined patterns of data being displayed on the one or more displays.

An embodiment of a method to detect SCC associated with pipeline joints of a longitudinally extending pipeline positioned to transport fluids associated with energy therethrough, for example, can include receiving, by one or more processors, magnetic flux leakage data from one or more pipeline inspection survey tools, the magnetic flux leakage data being associated with one or more joints of one or more longitudinal pipelines defining a pipeline joint, displaying, on or more displays, the magnetic flux leakage data as one or more selected patterns of data representing selected signal characteristics of the pipeline joint, analyzing, by one or more processors, the magnetic flux leakage data responsive to the selected signal characteristics and one or more predetermined patterns of the magnetic flux leakage data of the pipeline joint being displayed on the one or more displays, the one or more predetermined patterns of the magnetic flux leakage data being indicators of potential SCC associated with the pipeline joint, and determining, by one or more processors, a location of potential SCC associated with the pipeline joint responsive to the one or more predetermined patterns of magnetic flux leakage data being displayed on the one or more displays.

An embodiment of a computer implemented method to detect SCC associated with a pipeline can include receiving, by one or more processors, data associated with pipeline inspection, displaying, on or more displays, the data as one or more selected patterns of data representing selected signal characteristics of the pipeline, analyzing, by one or more processors, the data responsive to the selected signal characteristics and one or more predetermined patterns of the data of the pipeline being displayed on the one or more displays, the one or more predetermined patterns of the data being indicators of potential SCC associated with the pipeline, and determining, by one or more processors, a location of potential SCC associated with the pipeline responsive to the one or more predetermined patterns of data being displayed on the one or more displays.

An embodiment of a non-transitory storage medium having one or more computer programs stored thereon and readable by one or more processors, for example, can include one or more computer programs having a set of instructions that, when executed by the one or more processors, causes the one or more processors to perform the operations of: receiving magnetic flux leakage data from one or more pipeline inspection survey tools, the magnetic flux leakage data being associated with one or more joints of one or more longitudinal pipelines defining a pipeline joint, displaying the magnetic flux leakage data on the one or more displays as one or more selected patterns of data representing selected signal characteristics of the pipeline joint, analyzing the magnetic flux leakage data responsive to the selected signal characteristic and one or more predetermined patterns of the magnetic flux leakage data of the pipeline joint being displayed on the one or more displays, the one or more predetermined patterns of the magnetic flux leakage data being indicators of potential SCC associated with the pipeline joint, and determining a location of potential SCC associated with the pipeline joint responsive to the one or more predetermined patterns of magnetic flux leakage data being displayed on the one or more displays.

Embodiments of systems, methods, and computer media having computer programs, for example, can include an identification process developed through utilization of T-MFL inspection technology taken to a new level of sophistication with a disciplined methodical evaluation of data and data signals. Particularly, embodiments of the present invention can include supplemental screening processes applied to pipeline survey data, which utilize a T-MFL method and pattern recognition to identify potential SCC in welded pipe or other portions of one or more pipelines. The screening process of embodiments of the present invention does not need to affect or change how the survey data is recorded in the ILI survey tools or other pipeline inspection tools if that is not desired; only how it is analyzed after the collection of survey data is completed.

Embodiments of systems, methods, and computer media having computer programs of the present invention, can include confirmation and validation of the process applicability in each case. The confirmation will minimally consist of several validation excavations utilizing "highest level" Non-Destructive Evaluation ("NDE") methods and, in some cases, can require removal of appropriate samples for destructive metallurgical evaluation in a laboratory.

BRIEF DESCRIPTION OF DRAWINGS

The patent or application file contains at least one drawing executed in color. Copies of this patent or patent application publication with color drawing(s) will be provided by the Office upon request and payment of the necessary fee. Some of the features and benefits of the present invention having been stated, others will become apparent as the description proceeds when taken in conjunction with the accompanying drawings, in which.

DETAILED DESCRIPTION OF INVENTION

The present invention will now be described more fully hereinafter with reference to the accompanying drawings in which embodiments of the invention are shown. This invention may, however, be embodied in many different forms and should not be construed as limited to the illustrated embodiments set forth herein; rather, these embodiments are provided so that this disclosure will be thorough and complete, and will fully convey the scope of the invention to those skilled in the art. Like numbers refer to like elements throughout.

An embodiment of the present invention, for example, can include a supplemental screening process applied to survey data utilizing display software such as, for example, the ROSEN ROSOFT for Pipelines display software manufactured by the ROSEN Swiss AG of Stans, Switzerland (such as, for example, version 6.60), to identify potential SCC anomalies in pipelines. Another embodiment of the present invention, includes a supplemental screening process utilizing the GE-PII PipeImage inspection software. Although the present disclosure describes the present invention in conjunction with these software packages only, other forms of display software can be utilized as well as understood by those skilled in the art.

Figure 1:
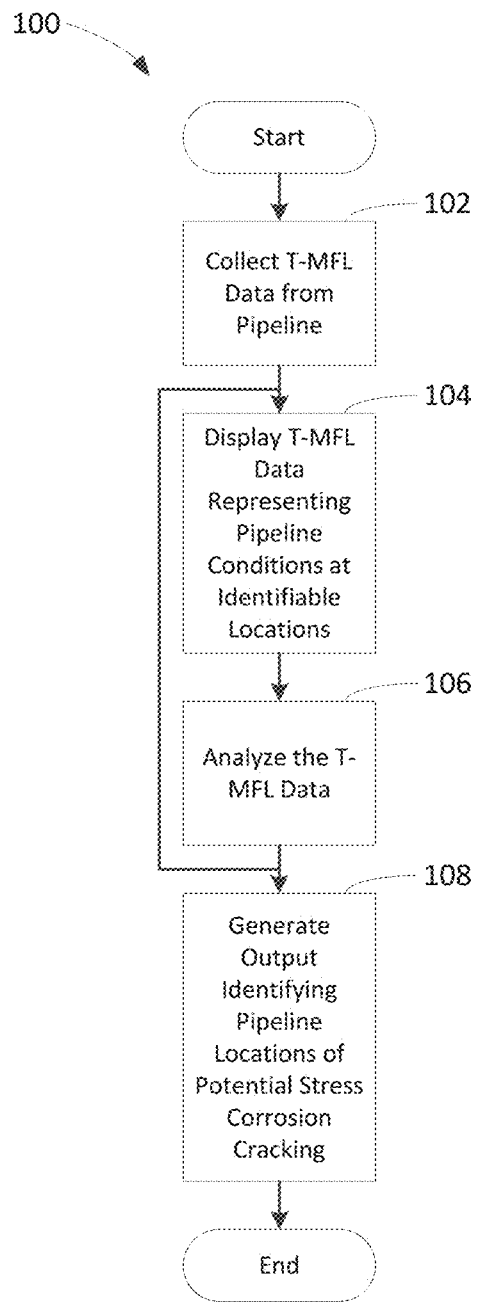
FIG. 1 is a flow chart illustrating one exemplary method including steps to determine locations having an elevated potential of SCC in one or more pipeline joints according to an embodiment of the present invention.
Figure 1A:
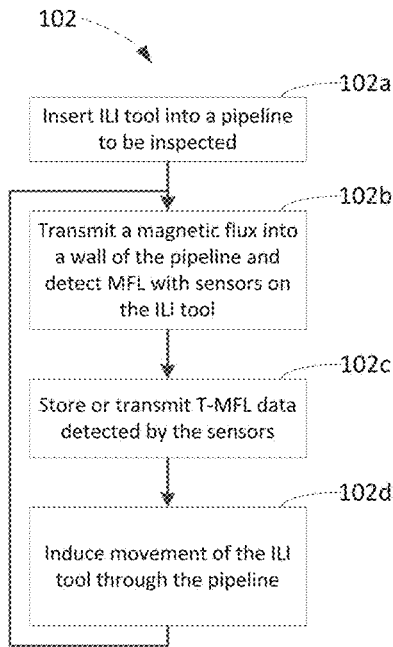
FIGS. 1A through 1D are flow charts illustrating examples of sub-steps of the steps illustrated in FIG. 1.

An embodiment of a method 100 of the present invention, such as shown in FIG. 1, can begin by collecting T-MFL data from a pipeline (step 102) using a survey tool, such as, for example, an ILI tool. The collection of data described in 102 is often performed by an inspection service provider such as ROSEN USA. In embodiments, step 102 can include sub-steps as identified in FIG. 1A. An ILI tool is inserted into a pipeline (step 102a) to create a magnetic circuit between the pipeline wall and the ILI tool. A magnetic flux is transmitted into a portion of the pipeline wall in the vicinity of the ILI tool, and sensors on the ILI tool such as Hall effect sensors detect any magnetic flux leakage from the pipeline wall (step 102b). The magnetic flux leakage detected can include leakage from longitudinal and circumferential welds of the pipeline, as well as leakage from all areas about a body of the pipeline wall. Signals detected by the sensors can include a component of a magnetic flux leakage vector that is transverse or orthogonal to an axis of the pipeline. The T-MFL data is primarily influenced by anomaly air gaps, which are a function of anomaly length and depth, steel properties, and hoop stress. The T-MFL data is either stored in an memory of the ILI tool that can be accessed once the ILI tool is removed from the pipeline, or the T-MFL data is transmitted to a computer (step 102c) having a processor (see, for example, processor 306 depicted in FIG. 18), as understood by those skilled in the art. Such a transmission can be achieved via any number of wired or wireless communications techniques. The circumferential and axial positions of the pipeline from which the T-MFL data is collected are noted such that the data can be correlated with a position pipeline position. The ILI tool is induced to move through the pipeline (step 102d) such that steps 102b and 102c can be repeated at every desired location along the pipeline. As one skilled in the art will recognize, steps 102b and 102c can be performed as the ILI tool is in motion.

At step 104, (FIG. 1) the processor then causes the T-MFL data to be displayed on a display as one or more patterns of data representing pipeline conditions at identifiable locations. The pipeline conditions displayed are based on T-MFL signal characteristics detected by the survey tool. In embodiments, step 104 can include sub-steps as identified in FIG. 1B. A portion of the collected data is selected for display (step 104a). The portion selected will usually correspond to a longitudinal length and circumferential section of the inspected pipeline. Suitable values for these parameters are influenced by the type of analysis to be performed, and in some embodiments can be selected with software controls as described in greater detail below with reference to FIGS. 12 and 13. Next, the manner in which the signal characteristics are represented in the display is selected (step 104b). As indicated in greater detail below, these signal characteristics can be displayed as, for example, smooth waveforms, contrasting colors, erratic/non-erratic patterns, or symmetrical patterns. Once the parameters are selected, the appropriate data is displayed (step 104c) on one or more displays (see, for example, displays 304 depicted in FIG. 18). Examples of data displayed in accordance with embodiments of the invention are depicted, for example in FIGS. 2-9 and 19-26. The displayed data can be viewed by an operator and modified and adjusted as necessary by repeating sub-steps 104a through 104c.

At step 106, (FIG. 1) the processor and/or operator will begin analyzing the T-MFL data based upon its respective signal characteristics. In embodiments, the analysis of step 104 can include sub-steps as identified in FIG. 1C. Initially, an advanced data analysis technique known as Kinder Morgan's KMAP process is performed by the processor (106a). Portions of the KMAP process are defined in Protocol PI 3, "KMAP Screening for Long Seam Anomaly Evaluation, ROSEN Software Package," and is generally employed in conjunction with a body scan and a longitudinal weld scan for evaluating the integrity of longitudinal welds in the pipeline. Other KMAP evaluations or related processes can be performed (step 106b) to evaluate circumferential welds, corrosion in a body of the pipeline and other inspection processes.

Figure 1B:
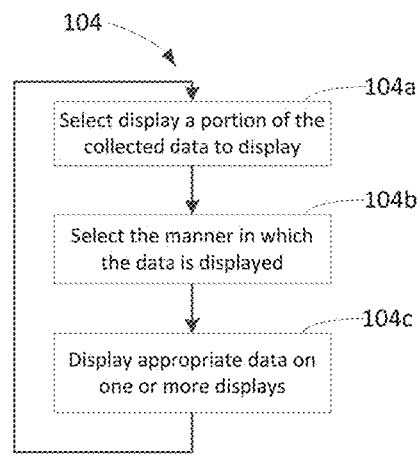
Figure 1C:
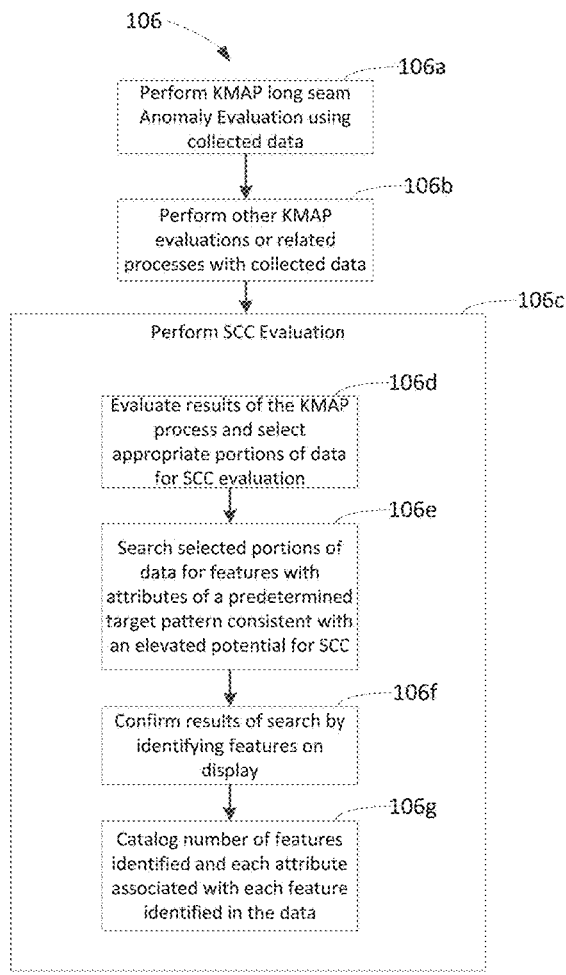

Based on the results of the KMAP Protocol, as understood by those skilled in the art, embodiments of systems, methods, and computer media having computer programs can additionally analyze circumferential MFL data, including C-Scan images, of pipe joints to determine if patterns indicative of potentially elevated risks of SCC are found to be contained in the data (step 106c). In embodiments, the results of the KMAP processes performed in steps 106a and 106b can be evaluated identify appropriate portions of data for SCC evaluation (step 106d). For example, portions of data associated with pipeline locations with elevated levels of corrosion may be identified by the KMAP process, and may be selected for SCC evaluation. Next, the selected portions of data can be searched for features (scratches, gouges, corrosion pits, etc.) that are associated with attributes of a predetermined target pattern consistent with an elevated potential for SCC (step 106e). Exemplary embodiments of attributes associated with a target pattern are discussed below, for example, with reference to FIGS. 3-9. In embodiments, the search is initially a computerized search performed by a computer processor. The results of the computerized search can be confirmed (step 106f) by an operator viewing the selected data displayed in step 104c (FIG. 1b). Once confirmed, the number of features identified in a particular set of selected data is cataloged, and each attribute of the target pattern associated with each of the identified features is cataloged (step 106g). A determination can then be made if the particular set of selected data is indicative of an elevated potential of for SCC. In embodiments, the particular set of selected data is graded as described with reference to FIG. 10 below.

Steps 104, 106 (FIG. 1) can be repeated for any number of sets of data. Thus, any number of sets of data corresponding to any number of pipeline locations can be displayed and analyzed.

Figure 1D:
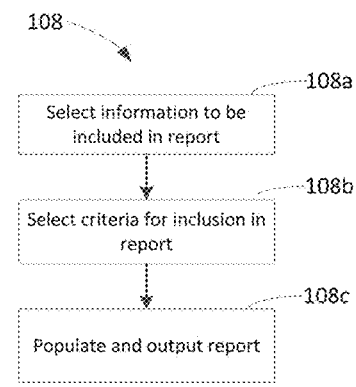

At step 108, an output is generated including a list of locations identified as being associated with a potentially elevated risk of SCC in the pipeline. In embodiments, step 108 can include sub-steps as identified in FIG. 1D. The information to be included in an output report can be selected (step 108a). This information can include, for example, the number of features identified in a particular set of data analyzed, the type of attributes identified, the time at which the data was collected, and other information as will be appreciated by those skilled in the art. Next, any desired criteria for inclusion in the output report can be selected (step 108b). For example, an operator may wish to include only the most likely candidate locations for SCC and may elect to include only those locations where 11 or more features were identified having attributes of the target pattern. In other instances, an operator may elect to include only locations where a particular attribute, a hook pattern (see FIG. 3) for example, was identified in the data. Next, the report is populated and output (step 108c) for review by an operator. Such an output can typically be a summary spreadsheet, associated screen captures and suggested excavation locations. The process 100 (FIG. 1) ends after step 108, although in other embodiments, such as in the method 200 described below with reference to FIG. 10, a method can be iteratively refined after excavating and evaluating one or more pipeline joints as recommended in the output generated in step 108.

Figure 2:
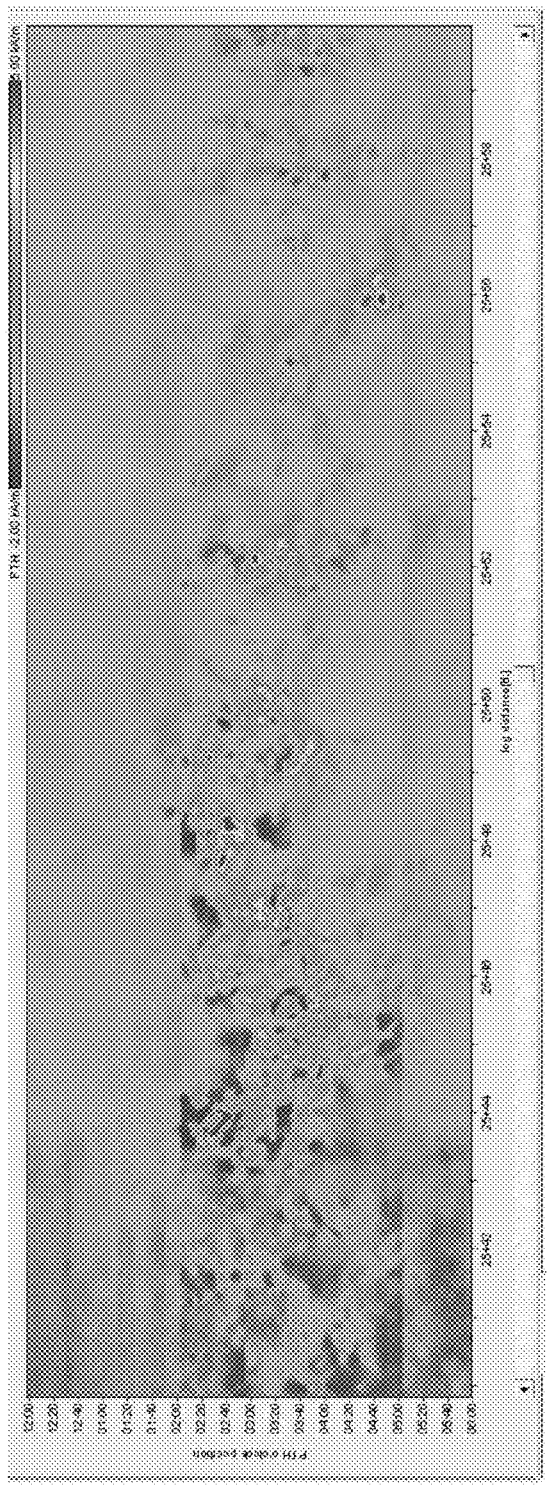
FIG. 2 is a colored graphical view of a C-Scan computer display showing the magnetic flux leakage data according to an embodiment of the present invention—the x-axis corresponds to an axial position (along a length of the pipeline) and the y-axis corresponds to an o'clock or radial position (around a circumference of the pipeline)

Referring now to FIG. 2, one example of a C-Scan computer display showing the MFL data from one pipeline location known to contain SCC is depicted. The pipeline location from which the data depicted in FIG. 2 was taken is Joint No. 550 in the Masonville to Tampico section of the 12-inch-diameter Cochin pipeline, which operates between Fort Saskatchewan, Alberta and Winsor, Ontario. The x-axis in FIG. 2 represents a longitudinal location along about 20 feet of the pipeline, and the y-axis represents a radial or circumferential location along about 20 circumferential inches of the pipeline wall. The color displayed at any particular location along these axes represents a characteristic of a T-MFL signal collected from the particular location. Red and yellow colors, for example, indicate signal characteristics associated with a greater degree of metal loss, while green and blue colors, for example, indicate signal characteristics associated with a relatively small degree of metal loss, or no discernible metal loss.

As a precaution, applicant undertook to evaluate the survey data to determine if SCC could be identified. There was no recognizable pattern in the detailed A-scan data (not shown), as understood by those skilled in the art. However the general appearance and nature of the features illustrated in the C-Scan image (FIG. 2) was thought to exhibit an identifiable target pattern, which could be recognized in data taken from other locations in a method of identifying locations with an elevated potential for SCC. The pattern of corrosion in Joint No. 550 is generally axial with some helical indications. Since the x-axis in C-Scan image of FIG. 2 represents a longitudinal distance along the pipeline, and the y-axis represents a circumferential location of the pipeline, the helical indications in the arrangement of the corrosion features appear diagonal in FIG. 2. The fact that corrosion is present means that a pipeline coating has failed and exposed the steel of the pipe body to the surrounding environment. Corrosion in pipelines starts with coating failure. Coating failure in turn exposes the steel of the pipe body to the surrounding environment. These factors can contribute to both corrosion growth and SCC development. The corrosion also indicates that the exposure had been in place for an extended period of time. The axial nature of the corrosion may mean it followed SCC or that SCC might have a preference to follow axially oriented corrosion. In this example, it was not known.

Based on these very general assumptions, applicant undertook to evaluate other joints in the Masonville to Tampico section of the Cochin pipeline to determine if a pattern similar to the target pattern of joint 550 could be recognized. Some of the pipe joints investigated and discussed herein were selected based on a gross pattern recognition technique wherein a target pattern consisting of generally axially aligned features as found in the pattern of signals representing joint 550 was identified. This pattern can still be a useful tool to locate pipe joints that should be given additional consideration for field investigation. This undertaking resulted in two (2) joints being identified (joints 610 and 26820) as having a corrosion pattern similar to the target pattern of joint 550. Through subsequent field investigations, joint 610 was found to contain SCC, and joint 26820 was found to not contain SCC.

Four (4) additional joints (joints 3000, 3210, 11780 and 18000) were identified as having some of the attributes of the target pattern of joint 550, but the patterns were not as similar as the patterns exhibited on joints 610 and 26820. These joints were reviewed in the field based on the results of the field investigation of joints 610 and 26820. Of these additional four (4) joints, three (3) were found to contain SCC (joints 3000, 11780 and 18000), while one (1) joint (joint 3210) was found to not contain SCC.

During the assessment of the joints from the Masonville to Tampico section of the Cochin pipeline discussed above, a final analysis of the Iowa City Lateral to Tampico portion of this pipeline was provided by an inspection service provider (ROSEN USA). There was one feature of interest immediately identified in joint 86070 (see FIG. 4). This feature was identified as metal loss with a maximum depth of 58% of a wall thickness of the pipeline. This feature was investigated in the field and found to be associated with SCC. Attributes of the corrosion pattern exhibited by joint 86070 were selected to enhance the target pattern. Thus, the investigation of further pipe joints for assessing the potential for SCC includes a comparison of the patterns of data relating to the further pipe joints with the attributes of the corrosion patterns exhibited by joints 550 and 86070.

One of the conclusions drawn from this initial assessment the T-MFL data gathered from several pipe joints of the Cochin pipeline is that, in some instances, signals indicative of elevated potentials for SCC are distinguishable from other signals represented in patterns of data displayed by software packages such as the ROSEN ROSOFT for Pipelines and GE-PII PipeImage software packages. In some cases where SCC is present (joint 550, in portion designated as SCC 02, for example), it may appear that signals or patterns are present that could represent the SCC anomaly. In other cases, portions of joint 550 designated as SCC 10 and SCC 13 for example, there is no apparent signal or pattern representing the SCC anomaly. In many areas, joint 550, SCC 05, for instance, the SCC location is so comingled with corrosion that it is not possible to discriminate any unique signal or pattern associated with the SCC anomaly. Similar examples can be found in the other pipe joints.

While in some cases it appears that a particular T-MFL signal detected at an SCC location is associated with a particular SCC anomaly, it cannot be assumed that there is a direct correlation. The ROSOFT for Pipelines software does not have enough resolution or operator features to make a direct determination of the presence of an SCC feature. In corrosion areas, the T-MFL signal generated and collected directly from an SCC anomaly is so comingled with much larger signals from the metal loss that any direct signal contribution from the SCC anomaly is lost. The GE PII PipeImage software initially may provide better imaging and resolution of TFI data than does the ROSOFT for Pipelines software and AFD data, even if neither software package reliably represents signals directly generated an SCC anomaly.

Figure 3:
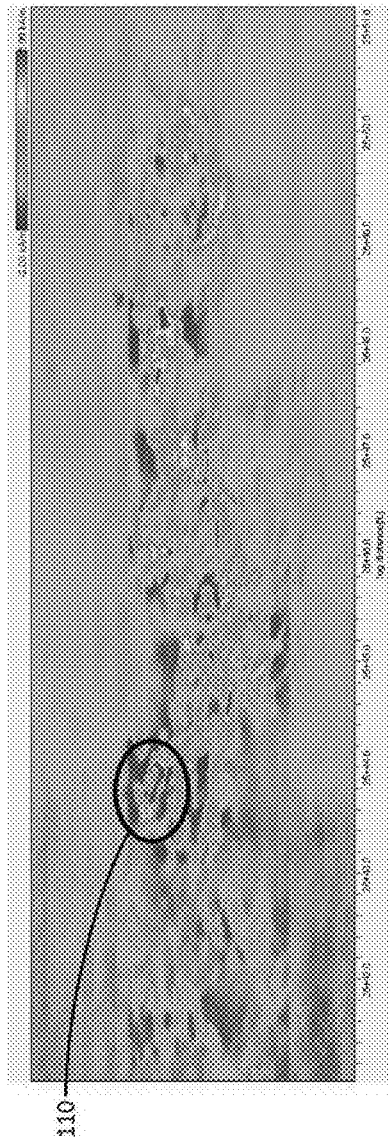
FIGS. 3-5 are colored graphical views of C-Scan computer displays generated from a first software tool (ROSEN ROSOFT for Pipelines Software Package) showing the magnetic flux leakage data collected from an inspection of pipeline joints known to include SCC anomalies.
Figure 4:
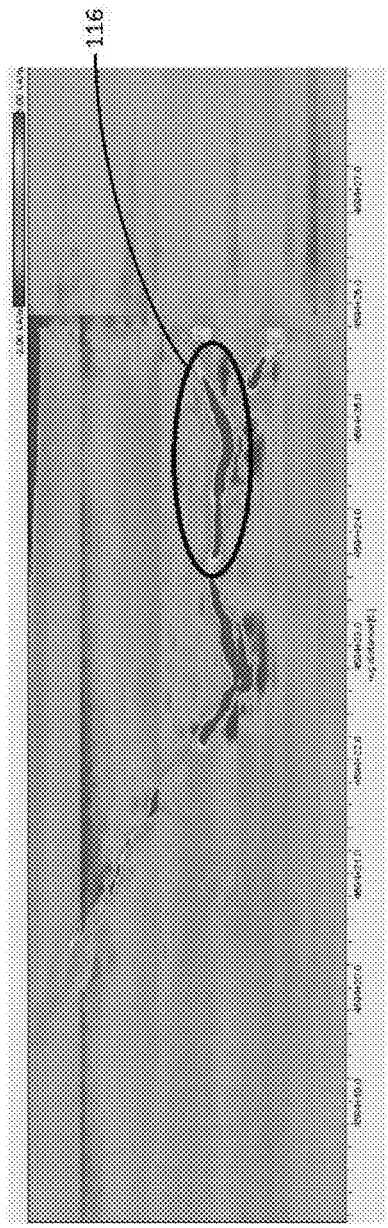

The development of a target pattern associated with some embodiments of the present invention is discussed herein with reference to FIGS. 3-9. FIGS. 3 and 4 represent foundation images from which the methods of the present invention were first developed. FIG. 3 is a C-Scan image generated by the ROSOFT for Pipelines software package representing AFD data collected over 10 axial feet and 180 circumferential degrees of joint 550 in the Masonville to Tampico section of the Cochin pipeline. The red and yellow colors representing the most significant corrosion are arranged in a generally axial pattern with a very slight diagonal extending upward and to the right. The slight diagonal represents a light indication of a helical corrosion pattern. An identifiable 'hook' shaped feature 110 appears within an area of significant corrosion, which may be an indicator of elevated potential for SCC. Thus, FIG. 3 defines at least three attributes of an identifiable target pattern for comparison with displayed images to assess whether the displayed images include indications of an elevated potential for SCC. These attributes include (1st) a generally axial arrangement of the colors indicating the most significant corrosion, (2nd) a diagonal arrangement of the colors indicating the most significant corrosion, and (3rd) a hook shaped feature identifiable in the corrosion pattern.

FIG. 4 is a C-Scan image generated by the ROSOFT for Pipelines software package representing AFD data collected over 10 axial feet and 180 circumferential degrees of joint 86070 in the Masonville to Tampico section of the Cochin pipeline. The colors indicating the most significant corrosion are again arranged in a generally axial pattern with a slight diagonal. A "worm" shaped feature 116 is an elongated undulating shape with generally tapered or rounded ends identifiable in the corrosion pattern. The worm shaped feature 116 represents a fourth (4th) attribute that may be included in a composite target pattern together with the three (3) attributes described above with reference to FIG. 3.

Figure 5:
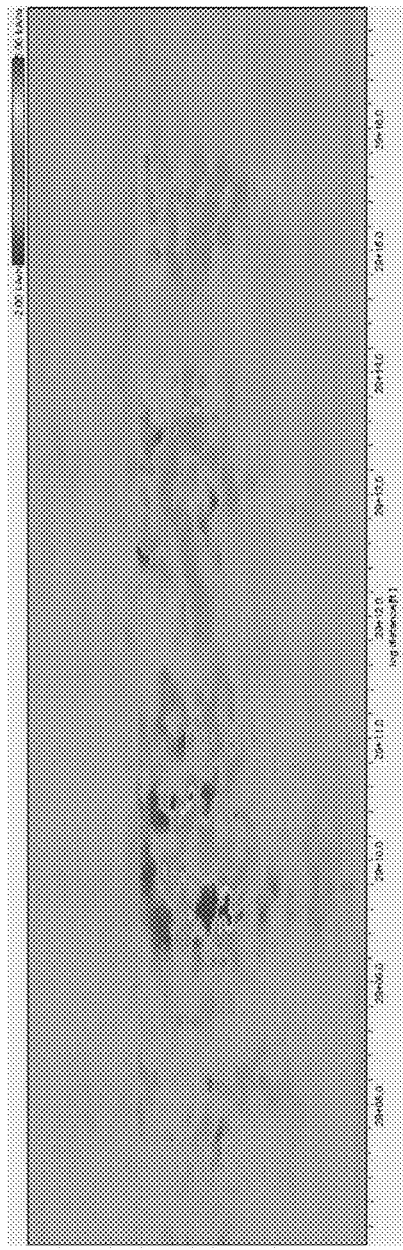
Figure 6:
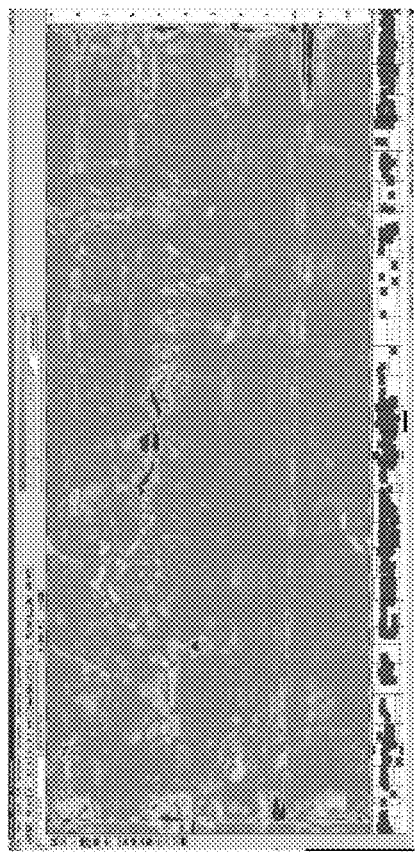
FIGS. 6-9 are colored graphical views of C-Scan computer displays generated from a second software tool (GE-PII PipeImage Software Package) showing the magnetic flux leakage data collected from an inspection of pipeline joints known to include SCC anomalies.
Figure 7:
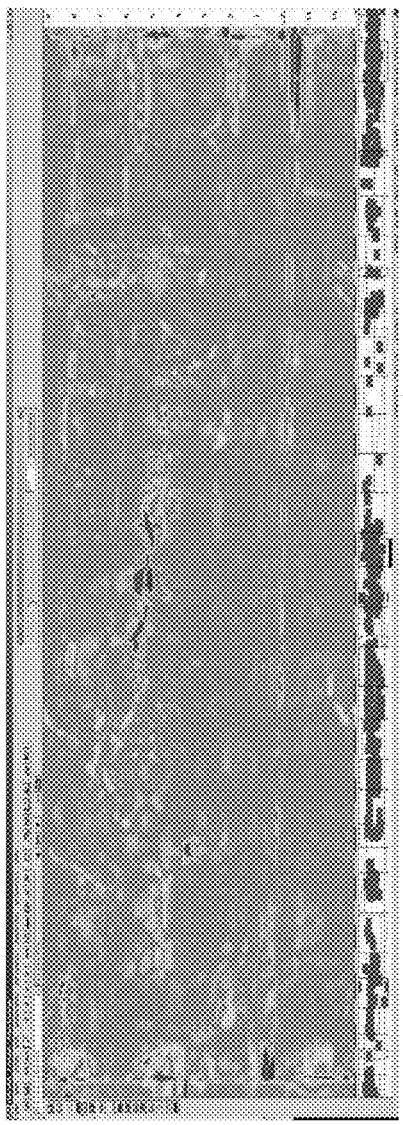

FIG. 5 is a C-Scan image generated by the ROSEN ROSOFT for Pipelines software package representing AFD data collected over 10 axial feet and 180 circumferential degrees of joint 610 in the Masonville to Tampico section of the Cochin pipeline. The colors indicating the most significant corrosion are again arranged in a generally axial pattern with a slight diagonal. However, the colors arranged in the axial pattern are generally green, rather than red and yellow as in FIGS. 3 and 4. The green color is an indicator that the corrosion is not as significant or severe as the corrosion represented in FIGS. 3 and 4, but since the corrosion patterns are similar, the pattern of corrosion illustrated in FIG. 5 is considered to be an indicator of elevated potential for SCC.

Figure 8:
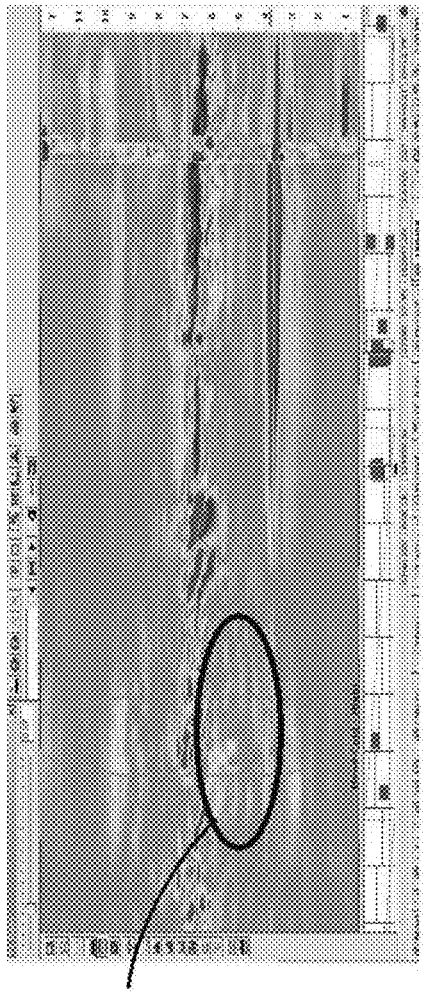
Figure 9:
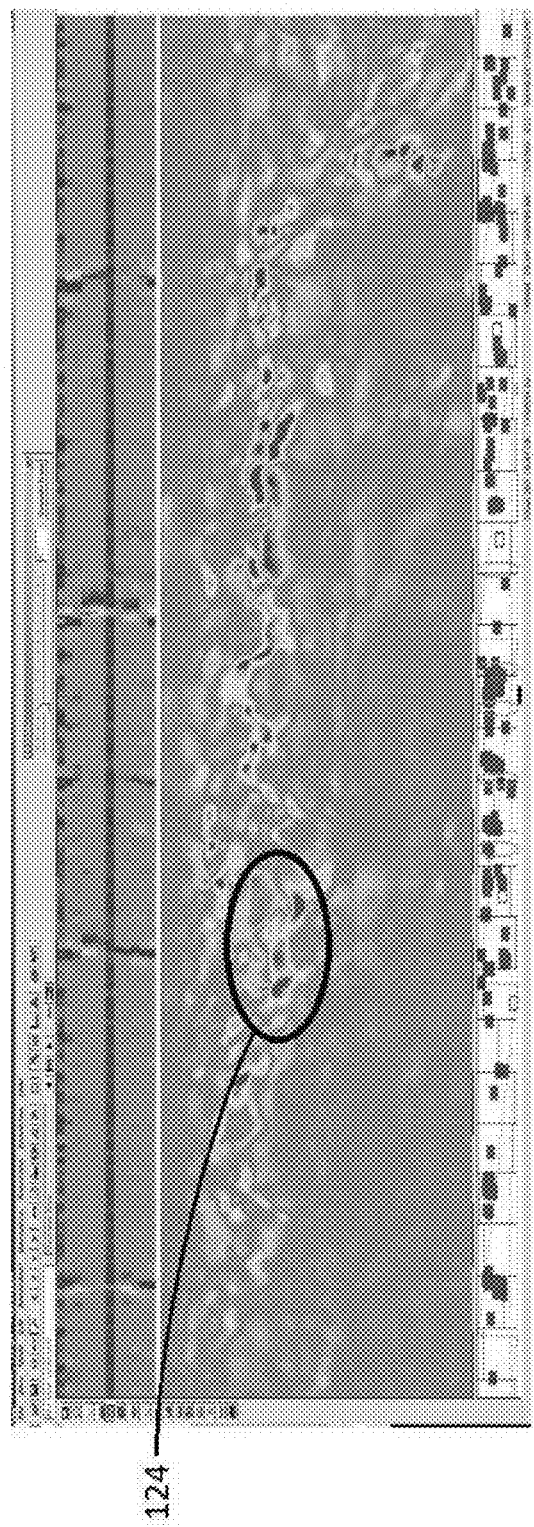

FIGS. 6-9 are C-Scan images generated by the GE-PII PipeImage software package representing TFI data collected over 360 circumferential degrees of respective joints 44540, 44530, 27280 and 70210 of the Rogers to Wheaton section of the Cochin Pipeline. The axial length over which the data was collected varies from 40 feet (FIG. 6), to 20 feet (FIGS. 7 and 9) and 10 feet (FIG. 8). In each of FIGS. 6-9, the colors indicating the most significant corrosion are again arranged in a generally axial pattern with a slight diagonal, and FIGS. 6 and 7 include identifiable "worm" shaped features as discussed above with reference to FIG. 4. FIG. 8 includes a "tiger-stripe" feature 120 with a congregation of repeating, circumferentially-spaced (vertically) narrow bands. A "tiger stripe" pattern represents a fifth (5th) attribute that may be included in a composite target pattern together with the four (4) attributes described above. FIG. 9 includes a "tree-bark" feature 124 where adjacent islands of a particular color are surrounded with a different color. The islands interlock with one another along the generally axial arrangement of colors indicating the most significant corrosion. The "tree-bark" pattern represents a sixth (6th) attribute that may be included in a composite target pattern together with the five (5) attributes described above.

Figure 10:
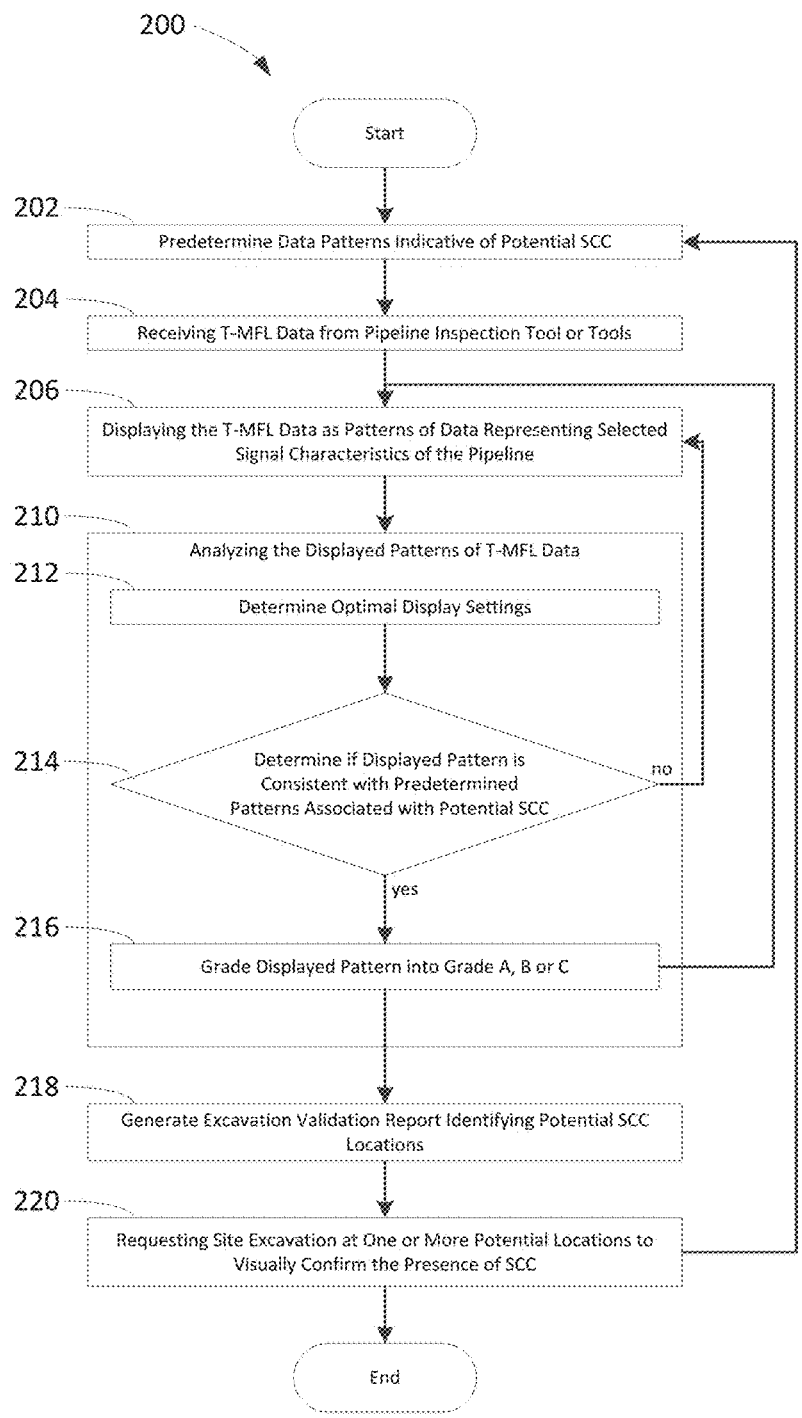
FIG. 10 is a flow chart illustrating steps of another exemplary method of determining locations having elevated potential of SCC in one or more pipeline joints according to an embodiment of the present invention.

Referring now to FIG. 10, an embodiment of a procedure 200 describes a supplemental screening process applied to ROSEN AFD or GE-PII TFI ILI survey data using the ROSEN ROSOFT for Pipelines or GE-PII PipeImage Display Software, as will be understood by those skilled in the art, to identify pipeline locations with an elevated potential of containing SCC. Aspects of this procedure 200, for example, can be called a "pattern recognition" process and may not be intended to directly detect SCC but rather the environmental and operating conditions that could lead to SCC development. The result of the pattern recognition process, for example, can be a ranking, e.g., subjective, of the anomalies based on relative signal characteristics.

An embodiment of this pattern recognition process or protocol, for example, identifies areas with an elevated risk of SCC. The application or use of this process, in some embodiments, can be sensitive to the pipeline steel properties, the coating condition of the pipeline, the operating environment of the pipeline, the capabilities of the specific pipeline inspection tool, survey tool or ILI tool employed, and the pipeline operating conditions under which the survey was conducted. Thus, when applying the pattern recognition protocol to other conditions, each variable may be considered and adjusted based on the specific application.

The process 200 begins with the predetermination of a target data pattern (step 202) that includes data patterns that are known or suspected to be associated with an elevated potential for SCC. The target pattern includes a plurality of identifiable attributes, such as an arrangement of features in a generally axial pattern representing the most significant corrosion in a particular display. In some embodiments, the predetermined target pattern is restricted to areas of corrosion identified by a pipeline inspection tool. The corrosion tends to be axial or longitudinal and has a slight helical indication. In some cases the pattern can be undulating or 'worm-like', while in other cases it can be more longitudinal. Both the ROSEN AFD tool and the GE-PII TFI tool display similar images of the target pattern Next, T-MFL data is received by a processor (step 204) from a pipeline inspection tool or tools. The inspection tool or tools may have been employed to conduct a pattern scan in conjunction with the KMAP weld scan and KMAP body scan described above. In 12-inch pipe, these scans can be done concurrently. In some embodiments, the T-MFL data includes data received from the ROSEN AFD tools and GE-PII TFI tools as described above. The T-MFL data is next displayed (step 206) by the processor on one or more displays, such as, for example an LCD computer screen. The T-MFL data is displayed as one or more selected patterns of data representing selected characteristics of a signal detected by the T-MFL tool from a wall of the pipeline. In some embodiments, the selected patterns of data include contrasting colors representing signal characteristics representative of a degree of metal loss in the pipeline wall as in the C-scan images of FIGS. 2-9 discussed above. In other embodiments, the selected patterns of data include smooth waveforms, erratic/non-erratic patterns, or symmetrical patterns for representing the selected signal characteristics. In some embodiments, the processor employs the ROSEN ROSOFT for Pipelines or GE-PII PipeImage Display Software to display the T-MFL data.

Once displayed, the T-MFL data is analyzed (step 210). The analysis includes a determination of optimal display settings (step 212), since different pipelines, for example, may require unique software or program product display values due to differences in magnetic characteristics, diameter, wall thickness, grade, and tool speed during the actual inspection, for example. Thus, step 210, in some embodiments, includes applying one or more pipeline variable characteristics to the magnetic flux leakage data being displayed on the one or more displays. The display software utilized as part of embodiments of the present invention, for example, can have an icon, button or other user interface on the display that, when clicked or operated, automatically sets the display values for optimum contrast. The processor then analyzes all the displayed data and responsively adjusts the values. This responsive setting, however, produces varying results depending on the amount of data displayed on the screen, for example, how long a section of pipe and how much of the pipe circumference is displayed.

Figure 11:
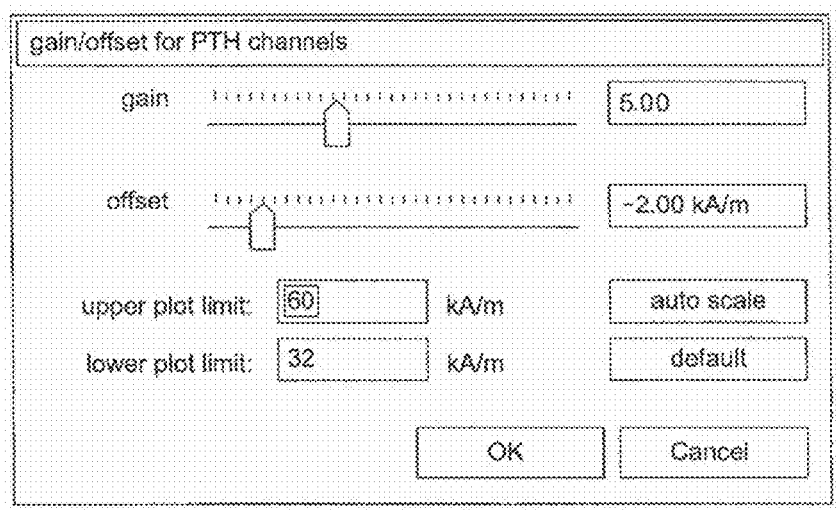
FIGS. 11-14 are graphical views of a display of a computer that show preferred display settings used to determine locations of potential SCC in one or more pipeline joints according to an embodiment of the present invention.

As illustrated in FIG. 11, one example display screen shows how the gain and offset of the T-MFL signals, can be manually sized to generate a high contrast display as part of the optimal display settings. In some embodiments, a non-erratic pattern can be distinguished from other patterns on a display when a gain is increased. The gain and offset values, in one embodiment, are set to 5 and −2 respectively using the ROSEN ROSOFT for Pipelines display software. Using the PipeImage display software, the default values for C-scan are employed along with a 'step size' of 1 and a smooth rainbow palette for producing high contrast images.

Figure 12:
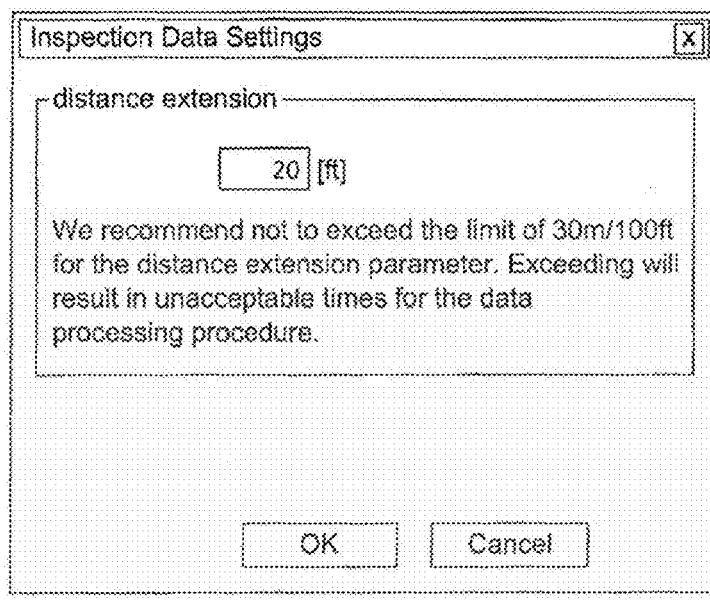

As illustrated in FIG. 12, embodiments of the present invention also allow the longitudinal length of pipeline data displayed (the length along the pipeline that the displayed data represents) to be set. In a preferred configuration using the ROSOFT for Pipelines, PipeImage or other display software packages, twenty (20) feet of pipeline data is displayed at one time. This display distance, however, can be adjusted to any desired length. Large values increase the time for the processor to load the T-MFL data, therefore memory and processor speed can determine the optimum number to select. The more data loaded at a time will increase the distance that can be reviewed before more data needs to be loaded.

Figure 13:
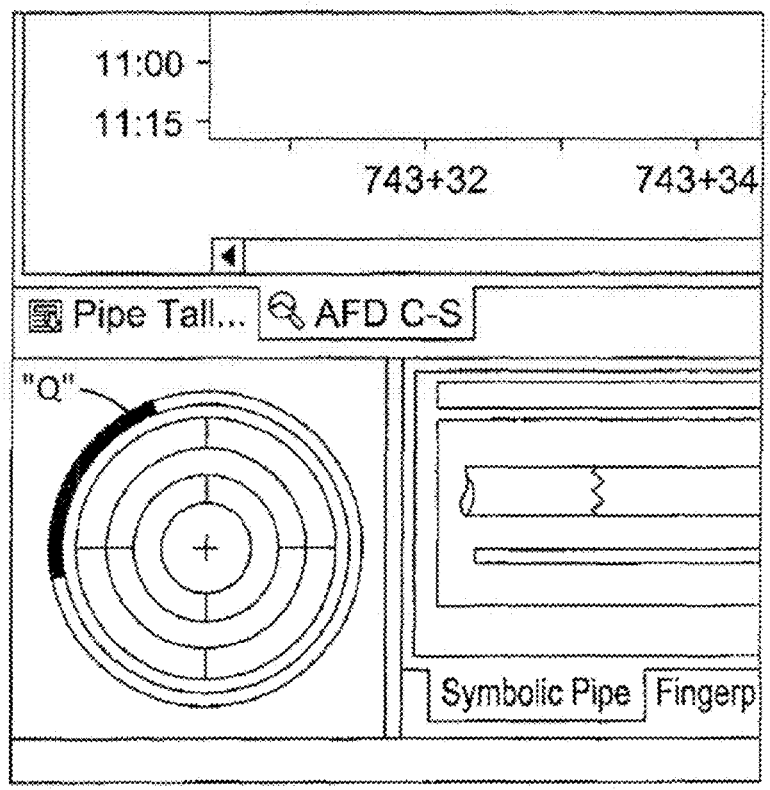

As illustrated in FIG. 13, a circumferential length of the pipeline displayed at one time may also be set. The quadrant section "Q" displayed in the outer ring can be rotated and/or expanded along its o'clock position, for example, by left-clicking the highlighted area of the outer ring and dragging it around. In some embodiments, a 360-degree view of the pipeline is selected.

Figure 14:
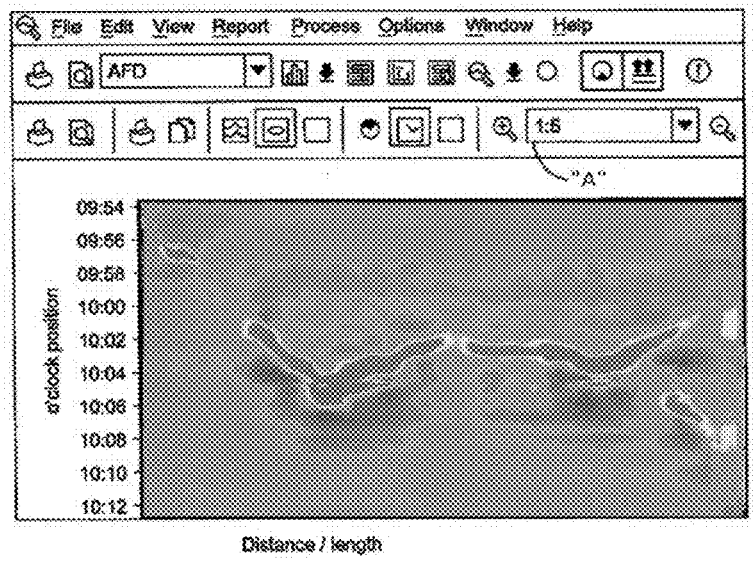

As illustrated in FIG. 14, an aspect ratio of the displayed data may also be set. A selection box "A" is available for setting an aspect ratio to reasonably view and assess the features of the displayed patterns of data.

Referring again to FIG. 10, once the presentation of the display has been optimized, a determination is made (step 214) if the displayed image of the patterns of data is consistent with target patterns of data, as determined in step 202, for example. To make this determination, an analyst may visually inspect the displayed image and assess the similarities and differences between the displayed image and the target pattern. For some embodiments of the present invention, analysts, operators or implementers performing an embodiment of a pattern recognition scan, as understood by those skilled in the art, desirably have some familiarity with pipelines, pipeline construction techniques, ILI tools and tool data and preferably have a working knowledge of pipeline inspection tools such as both PipeImage and ROSOFT for Pipelines software. In other embodiments, a processor makes an initial determination, and an analyst confirms the initial determination by viewing displayed patterns of data.

Figure 10A:
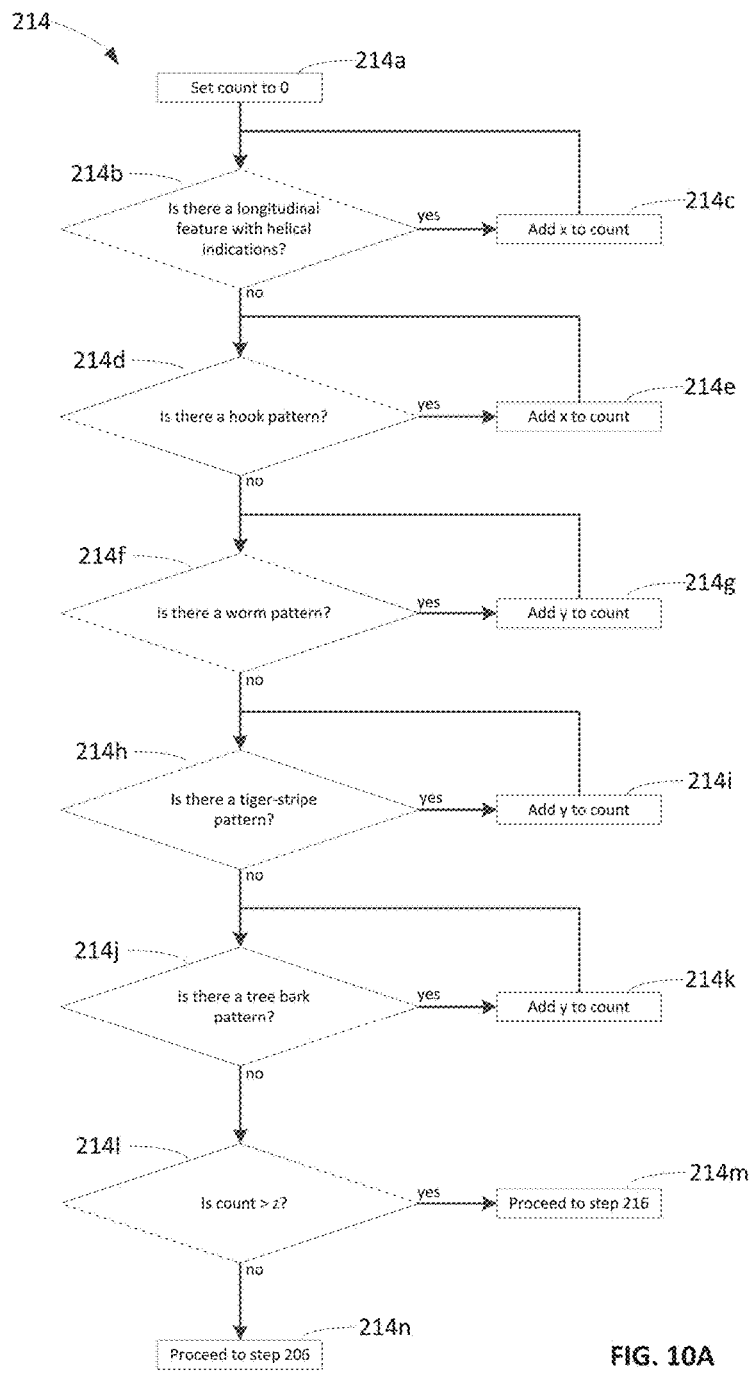
FIGS. 10A and 10B are flow charts illustrating example sub-steps of a determination step and a grading step of FIG. 10 respectively.

In some embodiments, the determination of step 214 can include the sub-steps identified in FIG. 10A. Initially, a variable "count" can be initialized to zero (step 214a). The variable count can be an indicator of how similar a displayed image is to the target pattern. A first determination is made (214b) if any longitudinal features with helical indications can be identified in the displayed image. If a longitudinal feature with helical indications is identified, a variable "x" is added to the variable count (step 214c). The process returns to step 214b to determine if there are additional longitudinal features with helical indications displayed. Thus, if there are three longitudinal features with helical indications displayed, for example, the variable count will increase by three times the variable x before proceeding to determine if any hook patterns are displayed (step 214d).

If any hook features are identified, the process proceeds to 214e to update the variable count before proceeding to determinations 214f, 214h and 214j to determine if any of these other attributes of the target pattern, i.e., a worm pattern, a tiger-stripe pattern, and a tree bark pattern, can be identified. Where these attributes are identified, the variable count is updated in steps 214g, 214h and 214k.

The variables "x" and "y" by which the count is updated can be assigned a value or weight according to how likely the corresponding attribute of the target feature is to indicate an elevated potential for SCC. For instance, in the illustrated embodiment, the variable "x" can be assigned a higher value than "y" where is determined that longitudinal features with helical indications and hook patterns are more likely to indicate an elevated potential for SCC than worm patterns, tiger-stripe patterns and tree bark patterns. Although only the variables "x" and "y" are illustrated in FIG. 10A, one skilled in the art will recognize that each attribute can be associated with an individual weight.

When all of the attributes have been counted, a determination is made whether the variable count is greater than a threshold value "z" (step 214l). Where the variable count is greater than the threshold value z, the displayed image is deemed to be consistent with predetermined patterns associated with an elevated potential for SCC (step 214m), and the procedure proceeds to step 216 (FIG. 10). Where the variable count is not greater than the threshold value z, the displayed image is deemed not to be consistent with predetermined patterns associated with an elevated potential for SCC (step 214n), and the procedure proceeds to step 206 (FIG. 10). In some embodiments, the threshold value z can be zero such that where the displayed image does include at least one of the attributes of the target pattern, the procedure proceeds to step 216 where the displayed pattern is graded A, B or C (step 216).

Figure 10B:
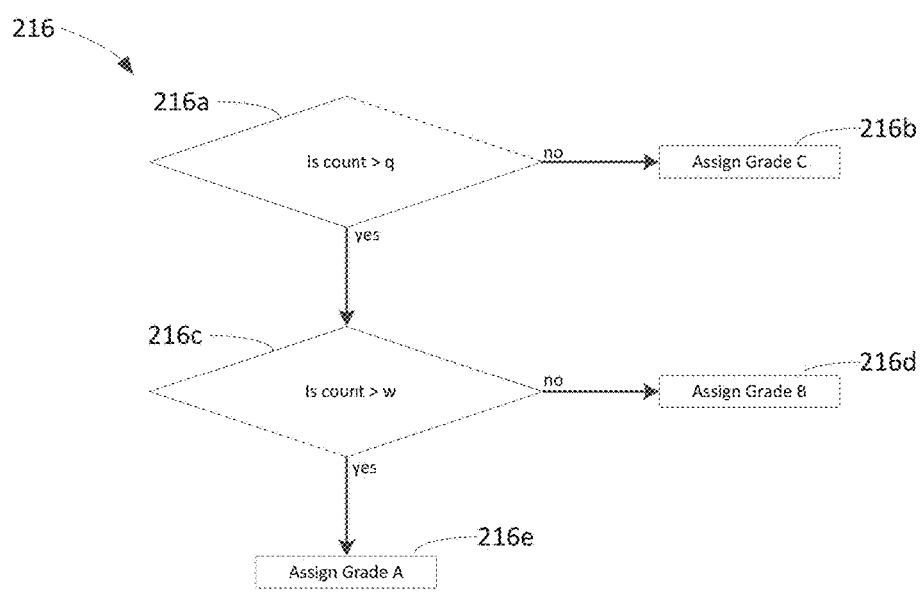

In some embodiments, the grading in step 216 can include the sub steps identified in FIG. 10B. Initially the variable "count," which was determined as described above with reference to FIG. 10A, is compared to a threshold variable "q" (step 216a). Where count is not greater than q, the displayed image is assigned a grade of "C" (step 216b) indicating that the displayed pattern has only passing resemblance to the target pattern. A grade of "C" can be an indicator that a joint could be considered for further evaluation in the event it were exposed and inspected for other reasons. Where count is greater than q, a determination is made whether the count is greater than a variable "w" (step 216c). Where count is not greater than w, the displayed image is assigned a grade of "B" (step 216d) indicating the pattern has some of the attributes of the target pattern representing a joint that could be considered for further assessment based on results obtained from any Grade A investigations. Where count is greater than w, the displayed image is assigned a grade of "A" (step 216e) indicating that the displayed pattern has all or most of the attributes of the target pattern representing a joint with a good potential of being associated with SCC. The variables "q" and "w" can be adjusted and modified according to any confirmation of the presence or absence of SCC resulting from visual inspection or metallurgical testing of a pipeline.

Referring again to FIG. 10, if it is determined in step 214 that the displayed image includes none of the attributes of the target pattern or is inconsistent with the target pattern, the process 200 continues to repeat step 206 and another image of patterns of data representing another location in the pipeline is displayed. The images to be displayed may be selected based on any desired criteria or algorithm. In some embodiments, when the ROSEN AFD data is being used the "Pipe Tally" will be used to locate or document the location pipe joints with four (4) or more features exhibiting attributes of the target pattern. In some embodiments, when GE-PII TFI data is being used the "Pipe Tally" will be used to identify pipe joints containing 11 or more features exhibiting attributes of the target pattern for evaluation.

Once each of the images selected for analysis is assessed and the appropriate images have been graded, an excavation validation report is generated (step 218) identifying locations potentially associated with an elevated potential for SCC. The excavation and validation report may include indications of the grades A, B or C assigned to the images so that a determination can be made whether a site excavation is appropriate for a particular location.

An embodiment of the pattern recognition process or protocol, as applied to this complex anomaly discrimination, should include and may require confirmation and validation of process applicability in each case. The confirmation can minimally include several validation excavations utilizing "highest level" NDE methods and, in some cases, may require removal of appropriate samples for destructive metallurgical evaluation in a laboratory. A site excavation is requested (step 220) for at least one of the locations identified in the excavation and validation report.

Figure 15:
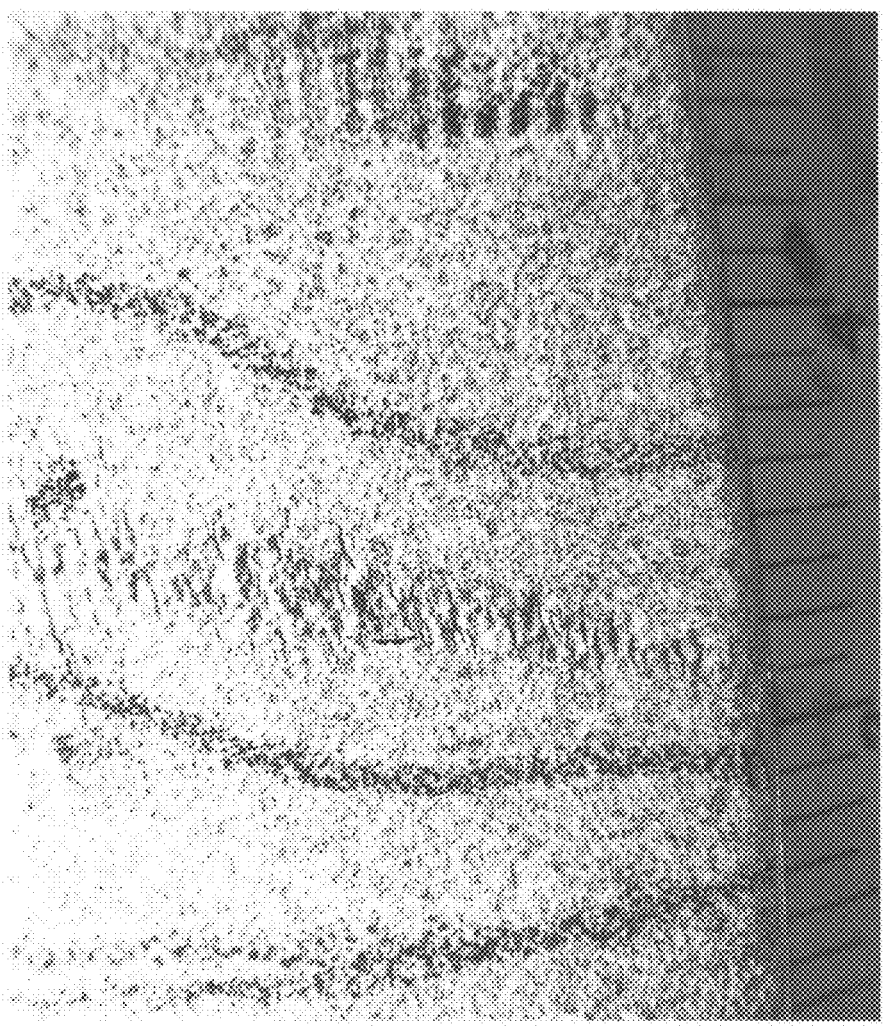
FIGS. 15-17 are photographic views of pipeline joints including corrosion anomalies including SCC.
Figure 16:
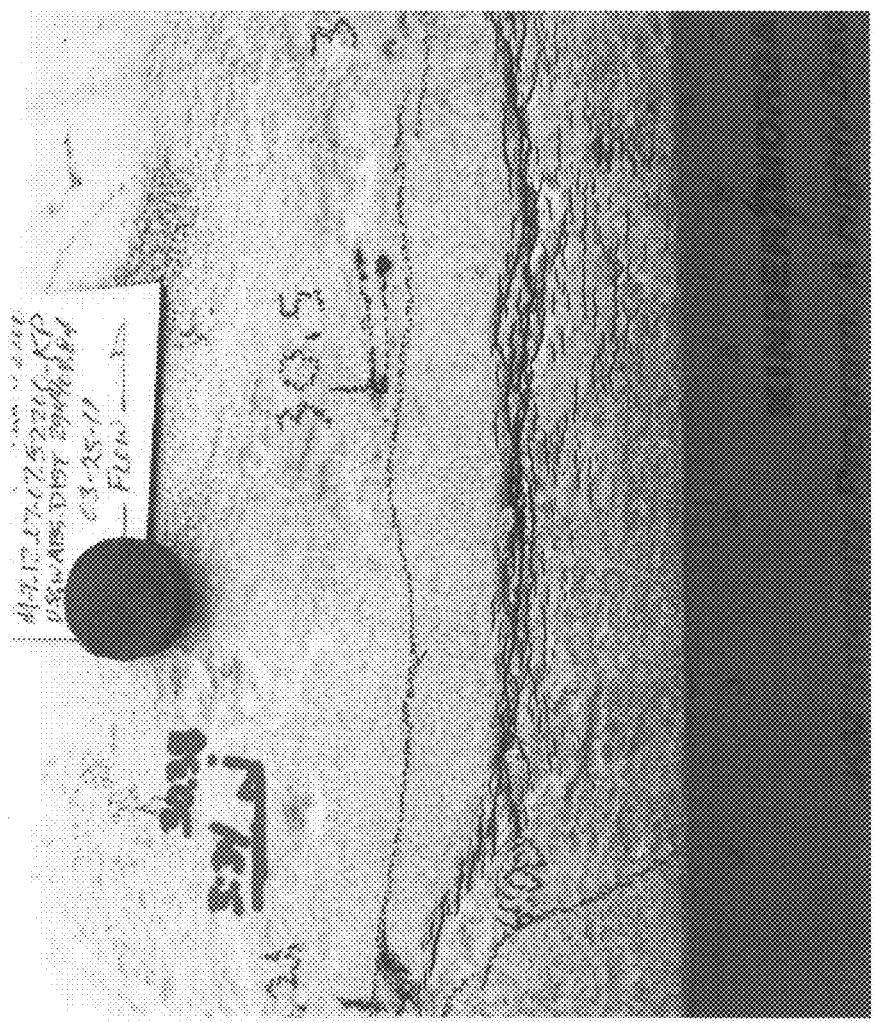
Figure 17:

Based on the results of any or several validation excavations performed, the predetermined patterns of data indicative of potential SCC may be refined as the process 200 returns to step 202. An auxiliary memory may be updated with excavation validation report data. Additional attributes may be added to the target pattern that are found to be present in the images representing the pipeline joints found to contain SCC, and attributes may be removed from the target pattern that were present in images representing pipe joints found not to contain SCC. As depicted in FIGS. 15-17, pipeline joints found to exhibit SCC included the corrosion features visible in these photographic images. The corrosion features are generally axial with a slight helical indication. Since these features represent some of the attributes of a target pattern discussed above, in other embodiments, photographic or other visual images of pipeline joints may be evaluated for the presence of attributes in a target pattern for assessing potential SCC. MFL tools are designed to find pipeline corrosion and present that information in both C-scan (Color density) and A-scan (line trace) views. Based on the experience and knowledge of KMAP personnel a visual pattern has been identified in the C-scan data view that may help identify areas susceptible to SCC. This technique is not a direct measurement or detection of the SCC itself but rather an overview of conditions that exist that could contribute to SCC development. In other embodiments, visual patterns may be identified in A-scan views that may help identify areas susceptible to SCC.

In all cases the results of field investigations can be reported to appropriate pipeline management personnel and can be compared to the assessment.

Also, the KMAP process can be assessed, evaluated and modified based on the field findings. For example, successful portions of the pattern recognition protocol described herein can be added to the KMAP process such that these portions are routinely associated with the KMAP process. This performance tracking can be an important feature of embodiments of the process.

Figure 18:
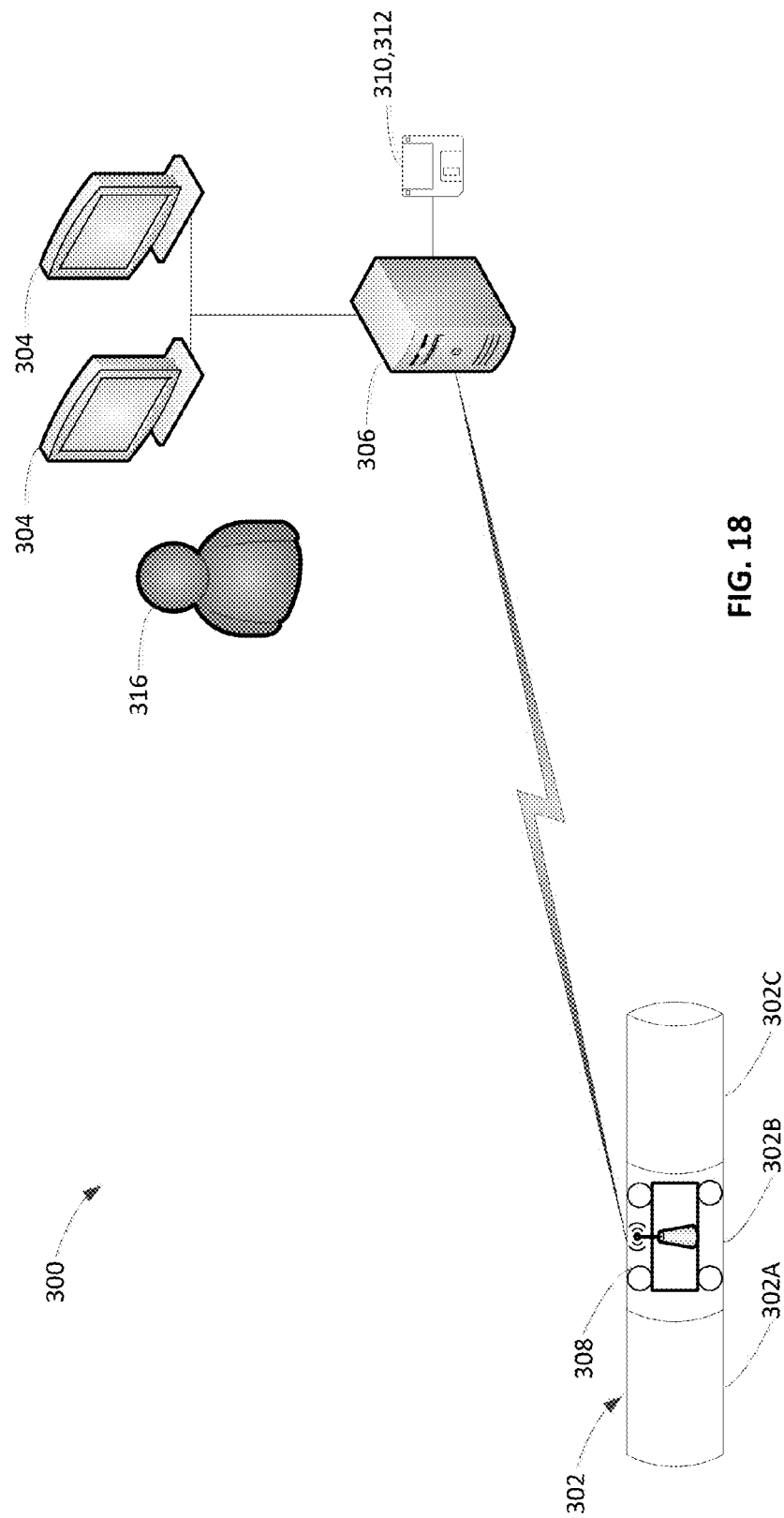
FIG. 18 is a schematic view of a system to detect potential SCC in one or more pipeline joints according to an embodiment of the present invention.
Figure 19:
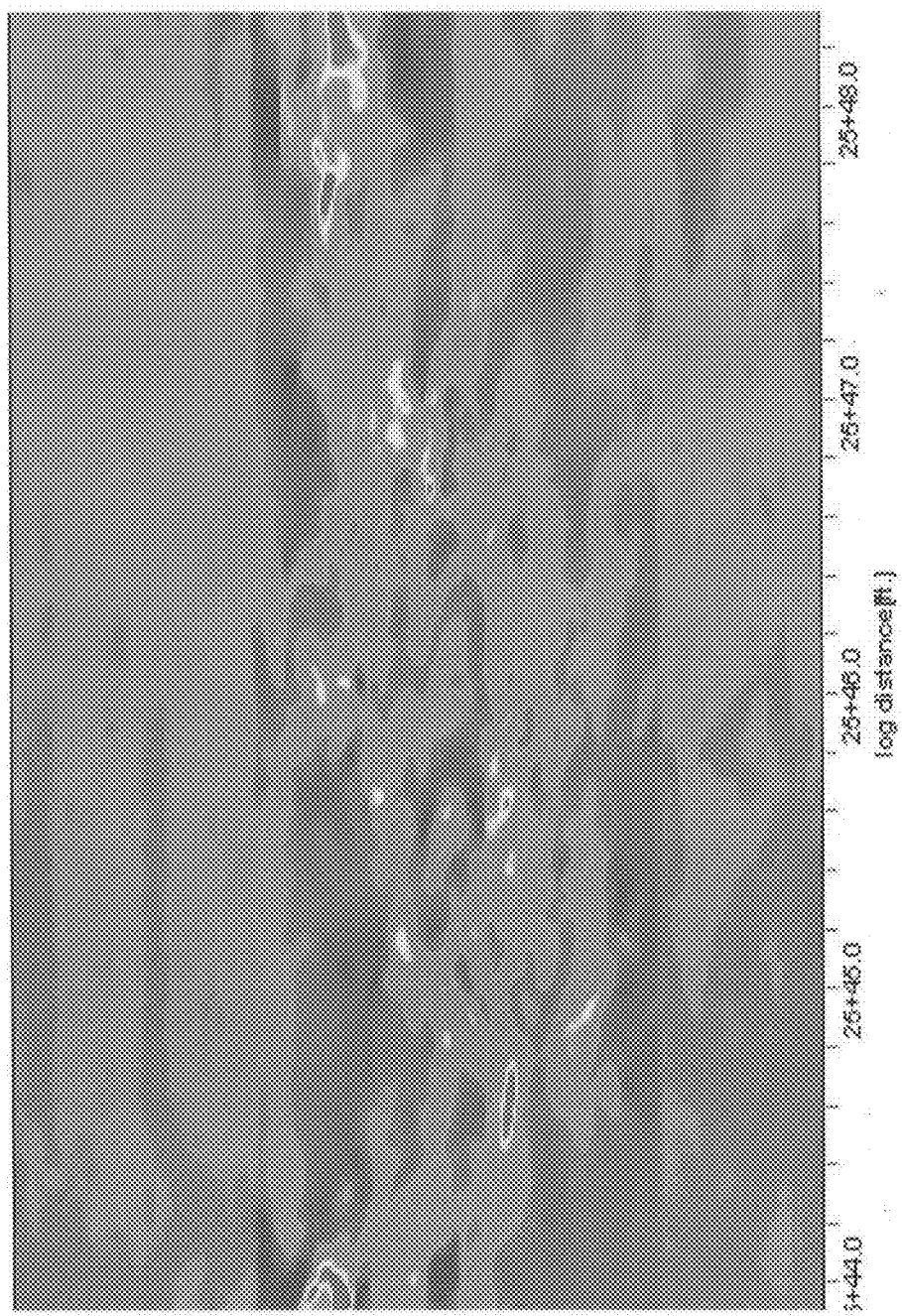
FIGS. 19-26 are close up colored graphical views of C-Scan images illustrating attributes of a target pattern used to determine locations of potential SCC in one or more pipeline joints according to an embodiment of the present invention.
Figure 20:
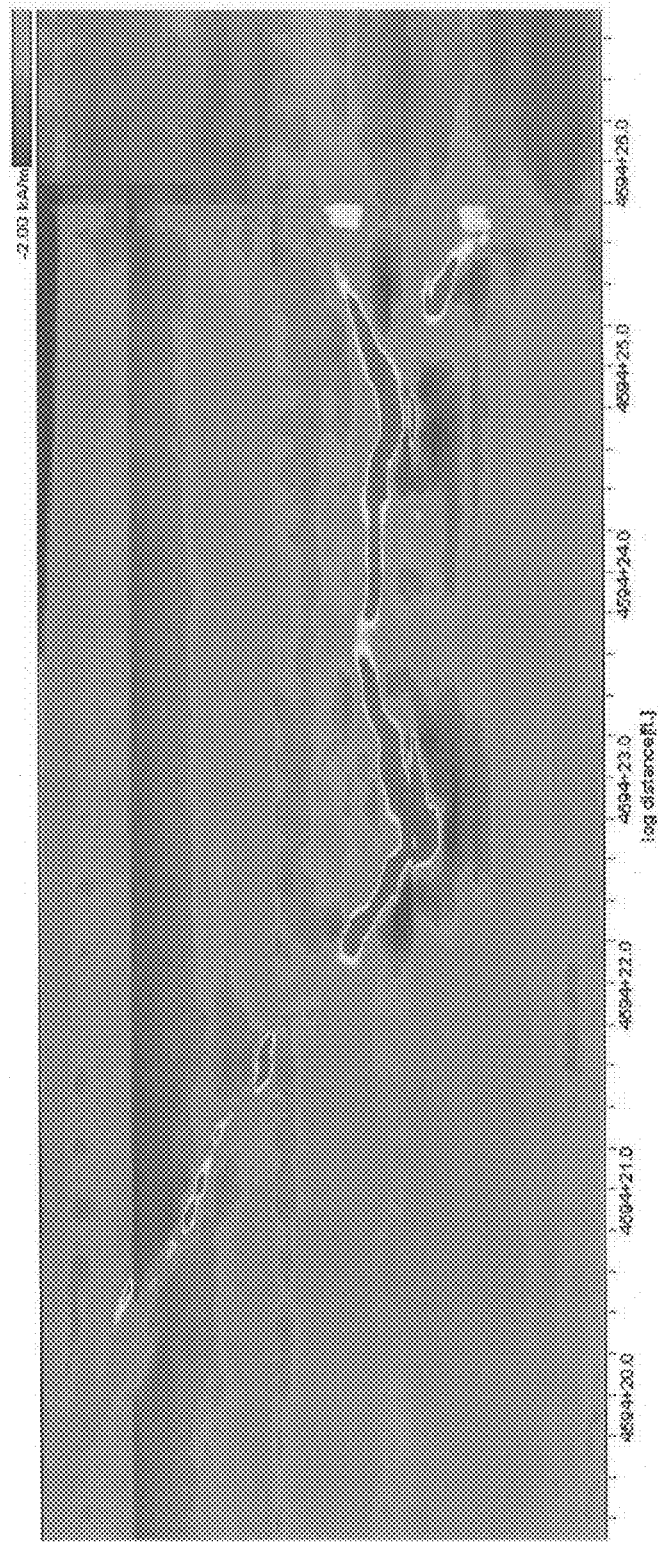
Figure 21:
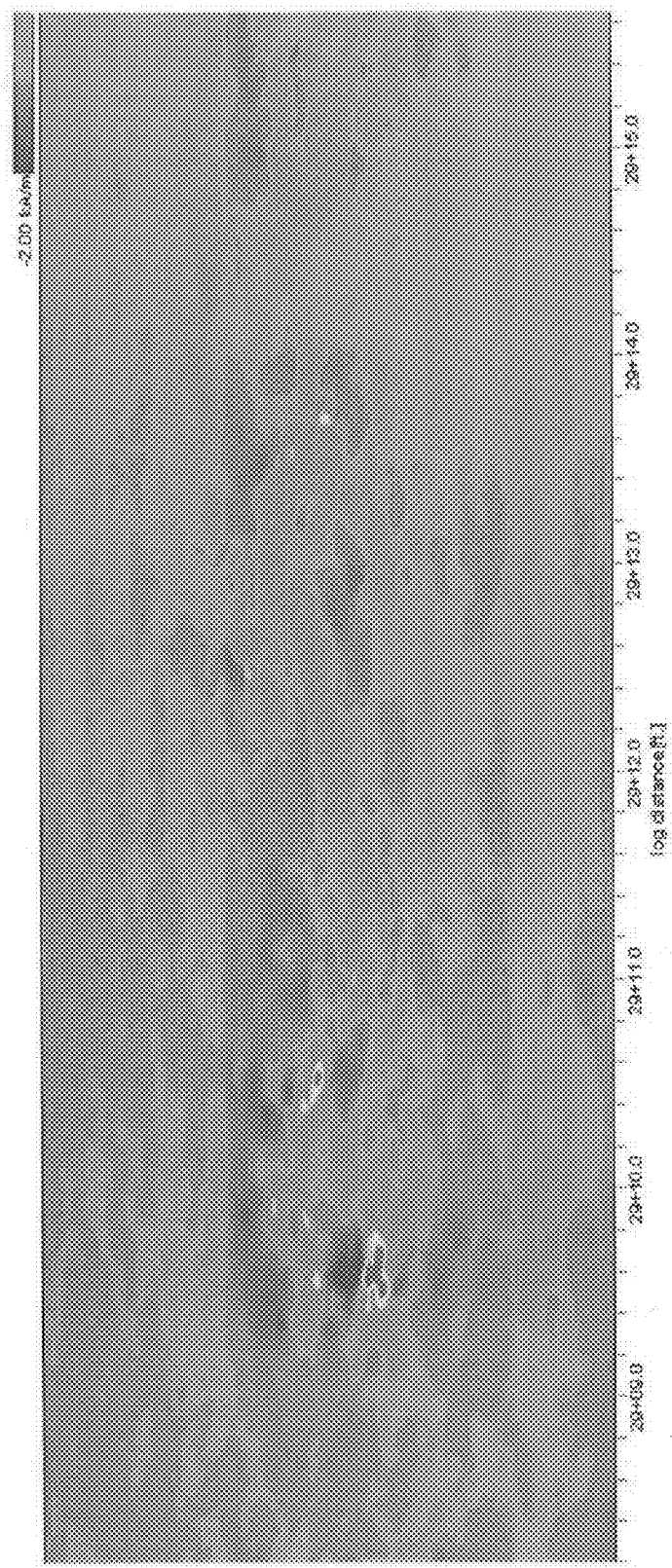
Figure 22:
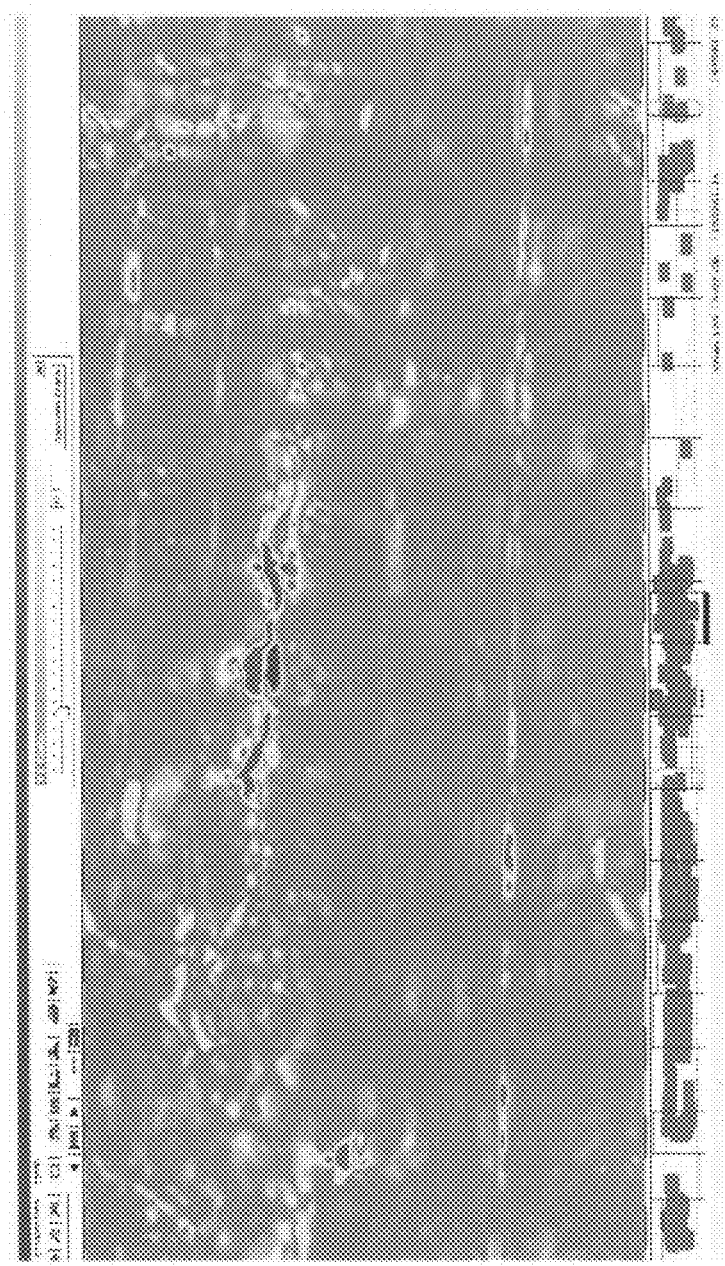
Figure 23:
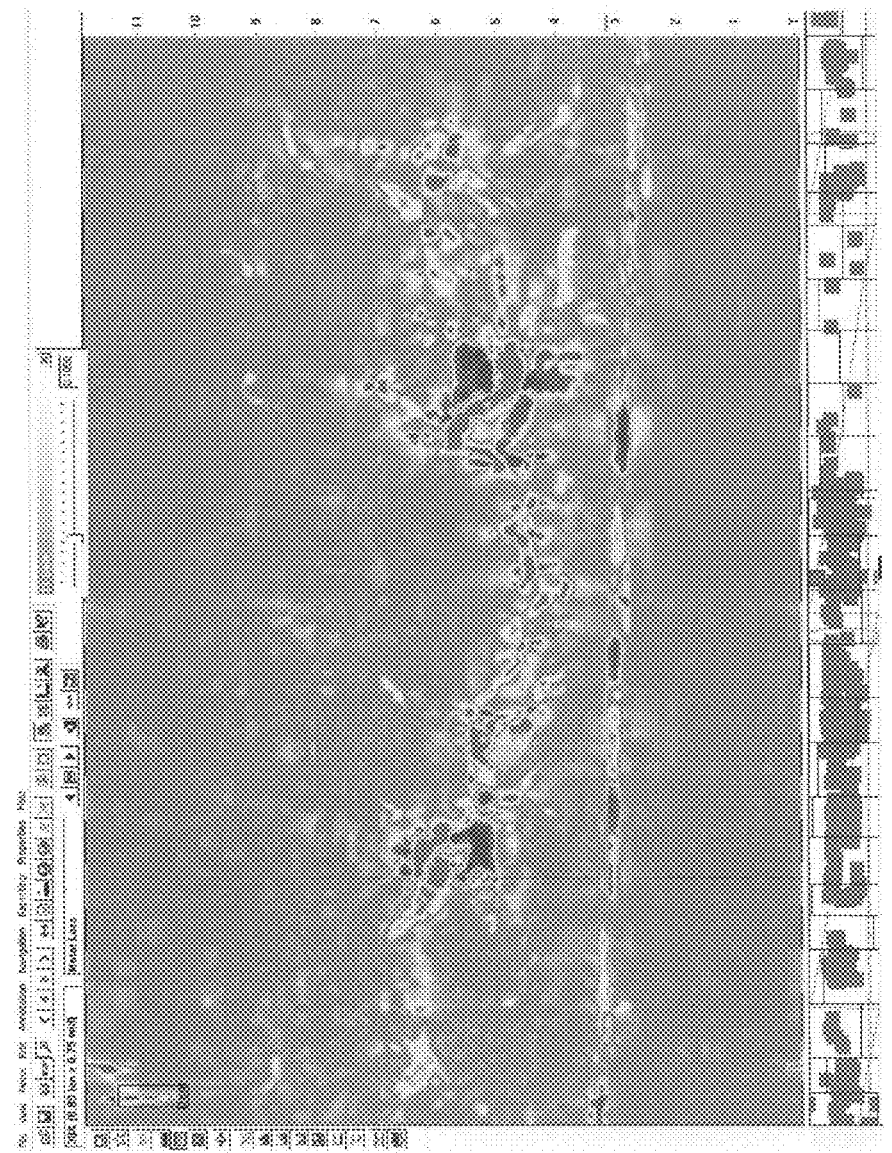
Figure 24:
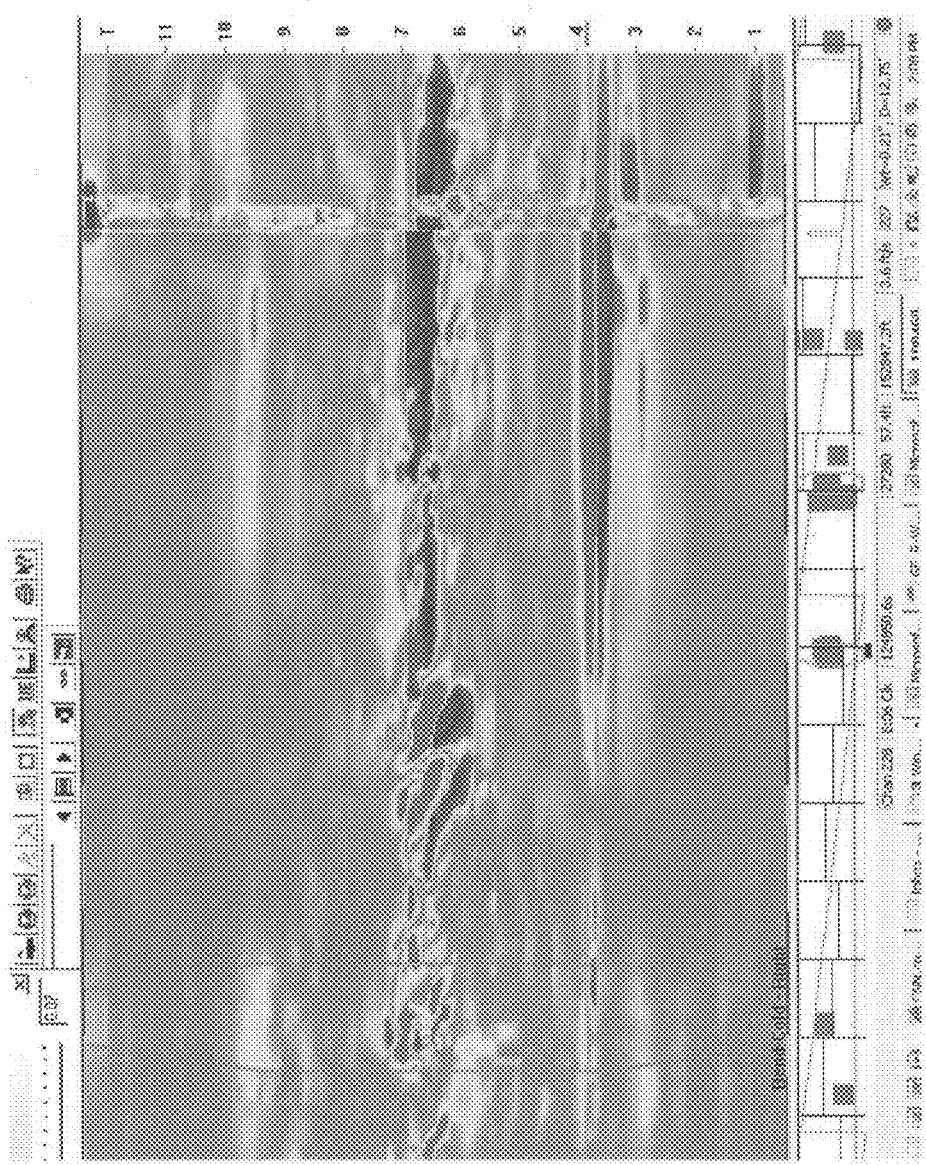
Figure 25:
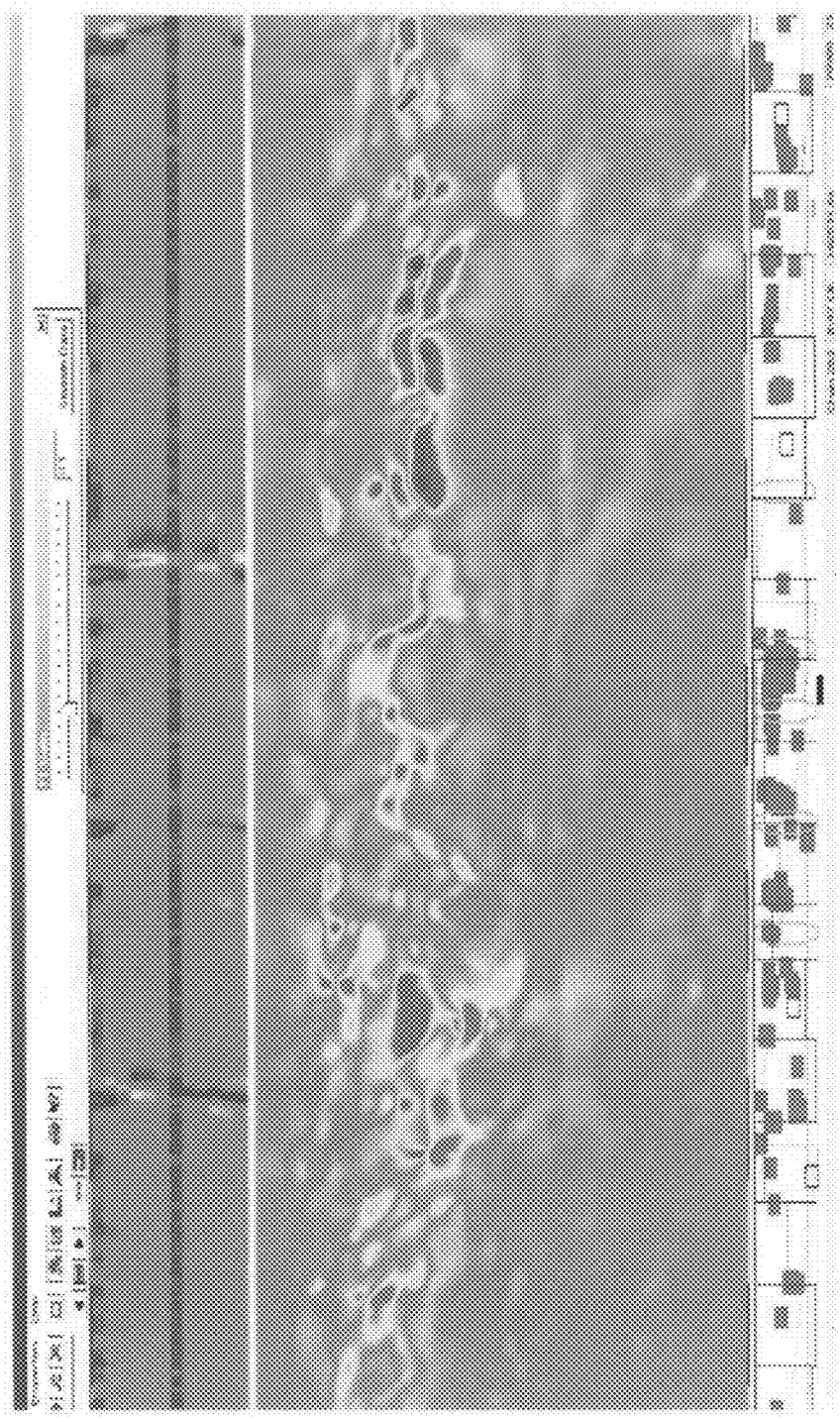
Figure 26:
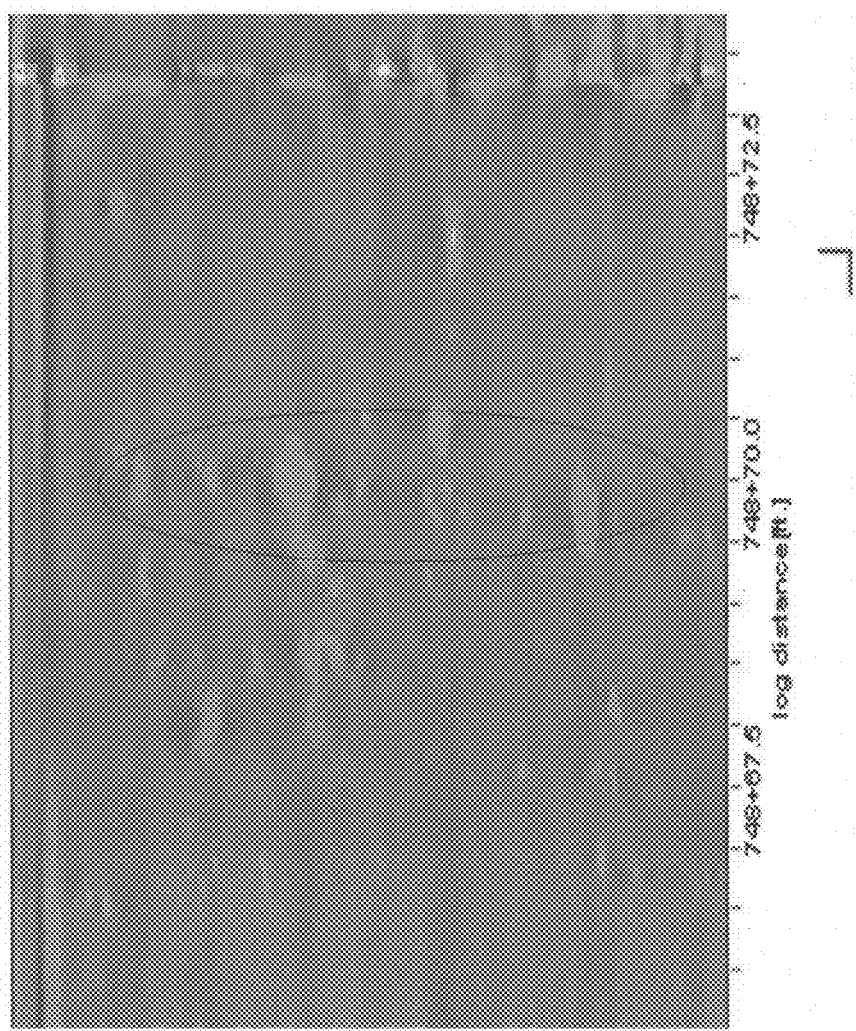

Referring now to FIG. 18, an embodiment of a system 300 to detect SCC associated with pipeline joints 302A, 302B, 302C of a longitudinally extending pipeline 302 positioned to transport fluids associated with energy therethrough, for example, is described. As used herein, the term "joints" is not restricted to locations within a pipeline wherein components come together such as longitudinal or circumferential welds, but includes larger subcomponents of a pipeline including sections of pipe. System 300 can include one or more displays 304, one or more processors 306 in communication with one or more pipeline inspection survey tools 308, and a non-transitory storage medium 310 or media having one or more computer programs stored thereon and readable by the one or more processors 306. The one or more computer programs can include a set of instructions that, when executed by the one or more processors 306, causes the one or more processors 306 to perform the operations of: receiving, in a first process, MFL data from the one or more pipeline inspection survey tools 308 related to the one or more joints 302A, 302B, 302C of one or more longitudinal pipelines 302 defining a pipeline joint 302B, for example, displaying, in a second process, the MFL data on the one or more displays 304 as one or more selected patterns of data representing selected signal characteristics of the pipeline joint 302B, analyzing, in a third process, the MFL data responsive to the selected signal characteristics and one or more predetermined patterns of the MFL data of the pipeline joint 302B being displayed on the one or more displays 304, the one or more predetermined patterns of the MFL data being indicators of potential SCC associated with the pipeline joint 302B, and determining, in a fourth process, a location of potential SCC associated with the pipeline joint 302B responsive to the one or more predetermined patterns of MFL data being displayed on the one or more displays 304. The system 300 includes an auxiliary memory 312 in communication with the one or more processors 306 to store report data to generate excavation validation report data. The auxiliary memory 312 may be updated with confirmation data including whether confirmation of the presence of SCC at an excavated site occurred thereby to further assess additional MFL data associated with the system 300.

In some embodiments, a user 316 such as an analyst can view the one or more displays 304 to assess and evaluate the one or more selected patterns of data displayed thereon to confirm a determination made by the processor in the fourth process. In other embodiments, the user 316 can facilitate the determination by providing an input to the one or more processors 306 based on an assessment made by viewing the one or more displays 304.

Another embodiment of a system to detect SCC associated pipeline, for example, can include one or more displays 304, one or more processors 306 in communication with the one or more displays 306, and a non-transitory storage medium 310 or media having one or more computer programs stored thereon and readable by the one or more processors 306. The one or more computer programs can include a set of instructions that, when executed by the one or more processors 306, causes the one or more processors 306 to perform the operations of: receiving, in a first process, data associated with an inspection of one or more pipelines 302, displaying, in a second process, the data on the one or more displays 304 as one or more selected patterns of data representing selected signal characteristics of the one or more pipelines 302, analyzing, in a third process, the data responsive to the selected signal characteristics and one or more predetermined patterns of the data of the one or more pipelines 302 being displayed on the one or more displays 304, the one or more predetermined patterns of the data being indicators of potential SCC associated with the one or more pipelines 302, and determining, in a fourth process, a location of potential SCC associated with the pipeline 302 responsive to the one or more predetermined patterns of data being displayed on the one or more displays 304.

An embodiment of a method to detect SCC associated with pipeline joints 302A, 302B, 302C of one or more longitudinally extending pipelines 302 positioned to transport fluids associated with energy therethrough, for example, can include receiving, by one or more processors 306, MFL data from one or more pipeline inspection survey tools 308, the MFL data being associated with one or more joints 302A, 302B, 302C of one or more longitudinal pipelines 302 defining a pipeline joint 302B, for example, displaying, on or more displays 304, the MFL data as one or more selected patterns of data representing selected signal characteristics of the pipeline joint 302B, analyzing, by one or more processors 306, the MFL data responsive to the selected signal characteristics and one or more predetermined patterns of the MFL data of the pipeline joint 302B being displayed on the one or more displays 304, the one or more predetermined patterns of the MFL data being indicators of potential SCC associated with the pipeline joint 302B, and determining, by one or more processors 306, a location of potential SCC associated with the pipeline joint 302B responsive to the MFL data being displayed on the one or more displays 304.

An embodiment of a computer implemented method to detect SCC associated with a pipeline 302 can include receiving, by one or more processors 306, data associated with pipeline inspection, displaying, on or more displays 304, the data as one or more selected patterns of data representing selected signal characteristics of the pipeline; analyzing, by one or more processors 306, the data responsive to the selected signal characteristics and one or more predetermined patterns of the data of the pipeline 302 being displayed on the one or more displays, the one or more predetermined patterns of the data being indicators of potential SCC associated with the pipeline 302, and determining, by one or more processors 306, a location of potential SCC associated with the pipeline 302 responsive to the one or more selected patterns of data being displayed on the one or more displays 304.

An embodiment of a non-transitory storage medium or media having one or more computer programs stored thereon and readable by one or more processors 306, for example, can include the one or more computer programs having a set of instructions that, when executed by the one or more processors 306, causes the one or more processors 306 to perform the operations of: receiving MFL data from one or more pipeline inspection survey tools 308, the MFL data being associated with one or more joints 302A, 302B, 302C of one or more longitudinal pipelines 302 defining a pipeline joint 302B, for example, displaying the MFL data on the one or more displays 304 as one or more selected patterns of data representing selected signal characteristics of the pipeline joint 302B, analyzing the MFL data responsive to the selected signal characteristics and one or more selected patterns of the MFL data of the pipeline joint 302B being displayed on the one or more displays 304, the one or more predetermined patterns of the MFL data being indicators of potential SCC associated with the pipeline joint 302B, and determining a location of potential SCC associated with the pipeline joint 302B responsive to the one or more selected patterns of MFL data being displayed on the one or more displays 304.

Embodiments of systems, methods, and computer media having computer programs, for example, can include an identification process developed through utilization of T-MFL inspection technology taken to a new level of sophistication with a disciplined methodical evaluation of data and data signals. Particularly, embodiments of the present invention can include supplemental screening processes applied to pipeline survey data, which utilize a T-MFL method and pattern recognition to identify potential SCC in welded pipe or other portions of one or more pipelines. The screening process of embodiments of the present invention does not need to affect or change how the survey data is recorded in the ILI survey tools if that is not desired; only how it is analyzed after the collection of the survey data is completed.

Embodiments of systems, methods, and computer media having computer programs of the present invention, can include confirmation and validation of the process applicability in each case. The confirmation will minimally consist of several validation excavations utilizing "highest level" NDE methods and, in some cases, can require removal of appropriate samples for destructive metallurgical evaluation in a laboratory.

It is to be understood by those skilled in the art that the invention is not limited to the exact details of construction, operation, exact materials, or embodiments shown and described, as modifications and equivalents will be apparent to one skilled in the art. For example, although discussed as steps in a computerized process, steps of the present invention may also be accomplished manually. In addition, although aspects of the present invention have been described with respect to a computer, a computer device, a computer system, or processor executing program product or software that directs the functions of embodiments of the present invention, it should be understood by those skilled in the art that the present invention can be implemented as a program product for use with various types of data processing systems as well. Programs defining the functions of embodiments of the present invention, for example, can be delivered to a data processing system via a variety of signal-bearing media, which include, without limitation, non-rewritable storage media (e.g., CD-ROM, DVD-ROM), rewritable storage media (e.g., floppy disks, hard drive disks, CD-R, or rewritable ROM media), and communication media, such as digital and analog networks. It should be understood, therefore, that such signal-bearing media, when carrying or embodying computer readable instructions that direct the functions of embodiments of the present invention, represent alternative embodiments of the present invention. In the drawings and specification, there have been disclosed illustrative embodiments of the invention and, although specific teens are employed, they are used in a generic and descriptive sense only and not for the purpose of limitation. Accordingly, the invention is therefore to be limited only by the scope of the appended claims.

That claimed is:

1. A system to detect stress corrosion cracking associated with pipeline joints of a longitudinally extending pipeline positioned to transport fluids associated with energy therethrough, the system comprising:
    one or more displays;
    one or more processors operable to be in communication with one or more pipeline inspection survey tools;
    one or more non-transitory storage medium having one or more computer programs stored thereon and readable by the one or more processors, the one or more computer programs including a set of instructions that, when executed by the one or more processors, causes the one or more processors to perform the operations of:
        determining a target pattern comprising an axial linear portion and a helical linear portion oriented diagonal to the axial linear portion, the axial linear portion corresponding to corrosion extending in a longitudinal direction along a length of a cylindrical pipeline, and the helical linear portion corresponding to corrosion extending in a helical direction about the cylindrical pipeline;
        receiving magnetic flux leakage data from the one or more pipeline inspection survey tools, the magnetic flux leakage data being associated with one or more joints of one or more longitudinal pipelines defining a pipeline joint;
        displaying the magnetic flux leakage data on the one or more displays as one or more selected patterns of data representing selected signal characteristics of the pipeline joint;
        analyzing one or more predetermined patterns of magnetic flux leakage data and the magnetic flux leakage data representing the selected signal characteristics of the pipeline joint being displayed on the one or more displays, the one or more predetermined patterns of the magnetic flux leakage data being indicators of potential stress corrosion cracking associated with the pipeline joint, the analyzing comprising comparing the target pattern to the one or more selected patterns to identify a selected pattern of the one or more selected patterns that is consistent with the target pattern;
        determining one or more locations of potential stress corrosion cracking associated with the pipeline joint responsive to the one or more predetermined patterns of magnetic flux leakage data being displayed on the one or more displays, the determining comprising determining a location of the selected pattern of the one or more selected patterns that is consistent with the target pattern;
        generating an excavation validation report identifying the one or more locations of potential stress corrosion cracking associated with the pipeline joint, the excavation validation report identifying the location of the selected pattern of the one or more selected patterns that is consistent with the target pattern; and
        generating a request for a site excavation for at least one of the locations of one or more potential stress corrosion cracking associated with the pipeline joint, the request for a site excavation requesting a site excavation at the location of the selected pattern of the one or more selected patterns that is consistent with the target pattern,
    wherein, responsive to the request, one or more site excavations are conducted to evaluate at least one of the locations of one or more potential stress corrosion cracking associated with the pipeline joint, the one or more site excavations comprising a site excavation at the location of the selected pattern of the one or more selected patterns that is consistent with the target pattern.

2. A system as defined in claim 1, wherein the determining the location of potential stress corrosion cracking includes identifying the presence of one or more patterns of the magnetic flux leakage data being displayed on the one or more displays that is consistent with the one or more predetermined patterns to identify the location of potential stress corrosion cracking in the pipeline joint.

3. A system as defined in claim 2, wherein the presence of the one or more patterns of the magnetic flux leakage data that is consistent with the one or more predetermined patterns is identifiable responsive to one or more optimal display settings, the one or more patterns of the magnetic flux leakage data that is consistent with the one or more predetermined patterns being representative of unique signal characteristics and being different than adjacent patterns representing adjacent signal characteristics being displayed on the one or more displays.

4. A system as defined in claim 3, wherein the one or more displays being one or more color displays, and wherein the one or more predetermined patterns being displayed are displayed as one or more colors that are different than colors of adjacent patterns representing signal characteristics on the one or more color displays.

5. A system as defined in claim 1, wherein the analyzing includes applying one or more pipeline variable characteristics to the magnetic flux leakage data being displayed on the one or more displays.

6. A system as defined in claim 1, wherein each of the one or more site excavations comprises a physical excavation and visual inspection of the pipeline joint at the location of the site excavation.

7. A system as defined in claim 6, further comprising auxiliary memory in communication with the one or more processors to store report data to generate the excavation validation report, wherein the set of instructions further causes the one or more processors to perform the operation of updating the auxiliary memory responsive to the one or more processors with confirmation data including whether confirmation of the presence of stress corrosion cracking at the excavated site occurred thereby to further assess additional magnetic flux leakage data associated with the system, and wherein the magnetic flux leakage data includes circumferential scan (C-scan) data of the pipeline joint.

8. A system as defined in claim 1, wherein the analyzing includes grading the selected patterns of magnetic flux leakage data displayed on the one or more displays into one or more grade levels, the one or more grade levels including a first grade level (Grade A) defined as including all or most of a set of attributes of the one or more of the predetermined patterns and representing a pipeline joint with a high potential of being associated with stress corrosion cracking.

9. A system as defined in claim 8, wherein the one or more grade levels includes the first grade level (Grade A), a second grade level (Grade B) defined as including some of the attributes of the one or more of the predetermined patterns and representing a pipeline joint to be considered for further assessment based on results from any investigations associated with the first grade level (Grade A), and a third grade level (Grade C) defined as having only passing resemblance to the one or more of the predetermined patterns and representing a pipeline joint to be considered for further evaluation if the pipeline joint were to be exposed and inspected for other reasons in the future.

10. A system as defined in claim 2, wherein the potential stress corrosion cracking has a location associated with the one or more predetermined patterns of the magnetic flux leakage data being displayed on the one or more displays comprising a non-erratic pattern being distinguished from other patterns on the one or more displays when a gain of the one or more selected patterns of the magnetic flux leakage data being displayed on the one or more displays is increased.

11. A system as defined in claim 2, wherein the analyzing step further comprises determining optimal display settings, and wherein the determining the optimal display settings comprises changing a gain and offset of the one or more patterns of the magnetic flux leakage data being displayed on the one or more displays in order to achieve a high contrast display so that the presence of the one or more predetermined patterns is perceptible on the one or more displays.

12. A system as defined in claim 11, wherein determining the optimal display settings further comprises:
    changing a longitudinal length along the pipeline that the selected patterns of data displayed on the one or more displays represents; and
    changing a circumferential length about the pipeline that the selected patterns of data displayed on the one or more displays represents.

13. A system as defined in claim 1, wherein the excavation validation report comprises a validation dig list containing one or more potential stress corrosion cracking locations, whereby the validation dig list facilitates identification of areas along the pipeline which are to be visually inspected for defects.

14. A system as defined in claim 1, wherein the pipeline is formed of steel, and wherein the one or more potential stress corrosion cracking locations is a function of one or more steel properties.

15. A system to detect stress corrosion cracking associated with pipeline, the system comprising:
    one or more displays;
    one or more processors being positioned to receive data from one or more pipeline inspection survey tools;
    one or more non-transitory storage medium having one or more computer programs stored thereon and readable by the one or more processors, the one or more computer programs including a set of instructions that, when executed by the one or more processors, causes the one or more processors to perform the operations of:
        determining a target pattern comprising an axial linear portion and a helical linear portion oriented diagonal to the axial linear portion, the axial linear portion corresponding to corrosion extending in a longitudinal direction along a length of a cylindrical pipeline, and the helical linear portion corresponding to corrosion extending in a helical direction about the cylindrical pipeline;
        receiving data from the one or more pipeline inspection survey tools, the data being associated with one or more pipelines;
        displaying the data on the one or more displays as one or more selected patterns of data representing selected signal characteristics of the one or more pipelines;
        analyzing one or more predetermined patterns of data and the one or more selected patterns of data representing the selected signal characteristics of the one or more pipelines being displayed on the one or more displays, the one or more predetermined patterns of the data being indicators of potential stress corrosion cracking associated with the one or more pipelines, the analyzing comprising comparing the target pattern to the one or more selected patterns to identify a selected pattern of the one or more selected patterns that is consistent with the target pattern; and
        determining one or more locations of potential stress corrosion cracking associated with the one or more pipelines responsive to the one or more predetermined patterns of data being displayed on the one or more displays, the determining comprising determining a location of the selected pattern of the one or more selected patterns that is consistent with the target pattern;

generating an excavation validation report identifying the one or more locations of potential stress corrosion cracking associated with the one or more pipelines, the excavation validation report identifying the location of the selected pattern of the one or more selected patterns that is consistent with the target pattern; and generating a request for a site excavation for at least one of the locations of one or more potential stress corrosion cracking associated with the one or more pipelines, the request for a site excavation requesting a site excavation at the location of the selected pattern of the one or more selected patterns that is consistent with the target pattern, wherein, responsive to the request, one or more site excavations are conducted to evaluate at least one of the locations of one or more potential stress corrosion cracking associated with the one or more pipelines, the one or more site excavations comprising a site excavation at the location of the selected pattern of the one or more selected patterns that is consistent with the target pattern.

16. A system as defined in claim 15, wherein the determining the location of potential stress corrosion cracking includes identifying the presence of one or more patterns of the data being displayed on the one or more displays that is consistent with the one or more predetermined patterns to identify the location of potential stress corrosion cracking in the one or more pipelines.

17. A system as defined in claim 16, wherein the presence of the one or more patterns of the data that is consistent with the one or more predetermined patterns is identifiable responsive to one or more optimal display settings, the one or more patterns of the data that is consistent with the one or more predetermined patterns being representative of unique signal characteristics and being different than adjacent patterns representing adjacent signal characteristics being displayed on the one or more displays.

18. A system as defined in claim 16, wherein the one or more displays are one or more color displays, and wherein the one or more predetermined patterns being displayed are displayed as one or more colors that are different than colors of adjacent patterns representing adjacent signal characteristics on the one or more color displays.

19. A system as defined in claim 15, wherein the analyzing includes applying one or more pipeline variable characteristics to the data being displayed on the one or more displays.

20. A system as defined in claim 15, wherein each of the one or more site excavations comprises a physical excavation and visual inspection of the one or more pipelines at the location of the site excavation.

21. A system as defined in claim 20, further comprising auxiliary memory in communication with the one or more processors to store report data to generate the excavation validation report, wherein the set of instructions further causes the one or more processors to perform updating the auxiliary memory responsive to the one or more processors with confirmation data including whether confirmation of the presence of stress corrosion cracking at the site being excavated occurred thereby to further assess additional data associated with the system, and wherein the data includes circumferential scan (C-scan) data of the one or more pipelines.

22. A system as defined in claim 15, wherein the analyzing includes grading the selected patterns of data displayed on the one or more displays into one or more grade levels, the one or more grade levels including a first grade level (Grade A) defined as including all or most of a set of attributes of the one or more of the predetermined patterns and representing portions of the one or more pipelines with a high potential of being associated with stress corrosion cracking.

23. A system as defined in claim 22, wherein the one or more grade levels includes the first grade level (Grade A), a second grade level (Grade B) defined as including some of the attributes of the one or more of the predetermined patterns and representing portions of the one or more pipelines to be considered for further assessment based on results from any investigations associated with the first grade level (Grade A), and a third grade level (Grade C) defined as having only passing resemblance to the one or more of the predetermined patterns and representing portions of the one or more pipelines to be considered for further evaluation if the portions of the one or more pipelines were to be exposed and inspected for other reasons in the future.

24. A system as defined in claim 15, wherein the potential stress corrosion cracking has a location associated with the one or more predetermined patterns of data being displayed on the one or more displays comprising a non-erratic pattern being distinguished from other patterns on the one or more displays when a gain of the one or more selected patterns of data being displayed on the one or more displays is increased.

25. A system as defined in claim 23, wherein the data includes magnetic flux leakage data, wherein the analyzing step further comprises determining optimal display settings, and wherein the determining the optimal display settings comprises changing a gain and offset of the one or more patterns of the magnetic flux leakage data being displayed on the one or more displays in order to achieve a high contrast display so that the presence of the one or more predetermined patterns is perceptible on the one or more displays.

26. A system as defined in claim 25, wherein determining the optimal display settings on the display further comprises:
changing a longitudinal length along the one or more pipelines that the selected patterns of data being displayed on the one or more displays represents; and
changing a circumferential length about the one or more pipelines that the selected patterns of data displayed on the one or more displays represents.

27. A system as defined in claim 16, wherein the excavation validation report comprises a validation dig list containing one or more potential stress corrosion cracking locations, whereby the validation dig list facilitates identification of areas along the one or more pipelines which are to be visually inspected for defects.

28. A system as defined in claim 25, wherein the pipeline is formed of steel, and wherein the one or more stress corrosion cracking locations is a function of one or more steel properties.

29. A method to detect stress corrosion cracking associated with pipeline joints of a longitudinally extending pipeline positioned to transport fluids associated with energy therethrough, the method comprising:
determining, by one or more processors, a target pattern comprising an axial linear portion and a helical linear portion oriented diagonal to the axial linear portion, the axial linear portion corresponding to corrosion extending in a longitudinal direction along a length of a cylindrical pipeline, and the helical linear portion corresponding to corrosion extending in a helical direction about the cylindrical pipeline;

receiving, by one or more processors, magnetic flux leakage data from one or more pipeline inspection survey tools, the magnetic flux leakage data being associated with one or more joints of one or more longitudinal pipelines defining a pipeline joint;

displaying, on or more displays, the magnetic flux leakage data as one or more selected patterns of data representing selected signal characteristics of the pipeline joint;

analyzing, by one or more processors, one or more predetermined patterns of magnetic flux leakage data and the magnetic flux leakage data representing the selected signal characteristics of the pipeline joint being displayed on the one or more displays, the one or more predetermined patterns of the magnetic flux leakage data being indicators of potential stress corrosion cracking associated with the pipeline joint, the analyzing comprising comparing the target pattern to the one or more selected patterns to identify a selected pattern of the one or more selected patterns that is consistent with the target pattern;

determining, by one or more processors, one or more locations of potential stress corrosion cracking associated with the pipeline joint responsive to the one or more predetermined patterns of magnetic flux leakage data being displayed on the one or more displays, the determining comprising determining a location of the selected pattern of the one or more selected patterns that is consistent with the target pattern;

generating, by one or more processors, an excavation validation report identifying the one or more locations of potential stress corrosion cracking associated with the pipeline joint, the excavation validation report identifying the location of the selected pattern of the one or more selected patterns that is consistent with the target pattern;

generating, by one or more processors, a request for a site excavation for at least one of the locations of one or more potential stress corrosion cracking associated with the pipeline joint, the request for a site excavation requesting a site excavation at the location of the selected pattern of the one or more selected patterns that is consistent with the target pattern; and conducting, responsive to the request, one or more site excavations to evaluate at least one of the locations of one or more potential stress corrosion cracking associated with the pipeline joint, the one or more site excavations comprising a site excavation at the location of the selected pattern of the one or more selected patterns that is consistent with the target pattern.

30. A method as defined in claim 29, wherein the determining the location of potential stress corrosion cracking includes identifying the presence of one or more patterns of the magnetic flux leakage data being displayed on the one or more displays that is consistent with the one or more predetermined patterns to identify the location of potential stress corrosion cracking in the pipeline joint.

31. A method as defined in claim 30, wherein the presence of the one or more patterns of the magnetic flux leakage data that is consistent with the one or more predetermined patterns is identifiable responsive to one or more optimal display settings, the one or more patterns of the magnetic flux leakage data that is consistent with the one or more predetermined patterns being representative of unique signal characteristics and being different than adjacent patterns representing adjacent signal characteristics being displayed on the one or more displays.

32. A method as defined in claim 31, wherein the one or more displays being one or more color displays, and wherein the one or more selected patterns being displayed are displayed as one or more colors that are different than colors of adjacent patterns representing signal characteristics on the one or more color displays.

33. A method as defined in claim 29, wherein the analyzing includes applying one or more pipeline variable characteristics to the magnetic flux leakage data being displayed on the one or more displays.

34. A method as defined in claim 29, each of the one or more site excavations comprises a physical excavation and visual inspection of the pipeline joint at the location of the site excavation.

35. A method as defined in claim 34, further comprising storing report data to generate the excavation validation report, updating, by one or more processors, confirmation data including whether confirmation of the presence of stress corrosion cracking at the excavated site occurred thereby to further assess additional magnetic flux leakage data associated with the method, and wherein the magnetic flux leakage data includes circumferential scan (C-scan) data of the pipeline joint.

36. A method as defined in claim 29, wherein the analyzing includes grading the selected patterns of magnetic flux leakage data displayed on the one or more displays into one or more grade levels, the one or more grade levels including a first grade level (Grade A) defined as including all or most of a set of attributes of the one or more of the predetermined patterns and representing a pipeline joint with a high potential of being associated with stress corrosion cracking.

37. A method as defined in claim 36, wherein the one or more grade levels includes the first grade level (Grade A), a second grade level (Grade B) defined as including some of the attributes of the one or more of the predetermined patterns and representing a pipeline joint to be considered for further assessment based on results from any investigations associated with the first grade level (Grade A), and a third grade level (Grade C) defined as having only passing resemblance to the one or more of the predetermined patterns and representing a pipeline joint to be considered for further evaluation if the pipeline joint were to be exposed and inspected for other reasons in the future.

38. A method as defined in claim 30, wherein the potential stress corrosion cracking has a location associated with the one or more predetermined patterns of the magnetic flux leakage data being displayed on the one or more displays comprising a non-erratic pattern being distinguished from other patterns on the one or more displays when a gain of the one or more selected patterns of the magnetic flux leakage data being displayed on the one or more displays is increased.

39. A method as defined in claim 30, wherein the analyzing step further comprises determining optimal display settings, and wherein the determining the optimal display settings comprises changing a gain and offset of the one or more patterns of the magnetic flux leakage data being displayed on the one or more displays in order to achieve a high contrast display so that the presence of the one or more predetermined patterns is perceptible on the one or more displays.

40. A method as defined in claim 39, wherein determining the optimal display settings further comprises:
changing a longitudinal length along the pipeline that the selected patterns of data displayed on the one or more displays represents; and
changing a circumferential length about the pipeline that the selected patterns of data displayed on the one or more displays represents.

41. A method as defined in claim 40, wherein the excavation validation report comprises a validation dig list containing one or more potential stress corrosion cracking locations, whereby the validation dig list is used to identify areas along the pipeline which are to be visually inspected for defects.

42. A method as defined in claim 29, wherein the pipeline is formed of steel, and wherein the one or more stress corrosion cracking locations is a function of one or more steel properties.

43. A computer implemented method to detect stress corrosion cracking associated with pipelines, the method comprising:
determining, by one or more processors, a target pattern comprising an axial linear portion and a helical linear portion oriented diagonal to the axial linear portion, the axial linear portion corresponding to corrosion extending in a longitudinal direction along a length of a cylindrical pipeline, and the helical linear portion corresponding to corrosion extending in a helical direction about the cylindrical pipeline;
receiving, by one or more processors, data associated with one or more pipelines;
displaying, on one or more displays, the data as one or more selected patterns of data representing selected signal characteristics of the one or more pipelines;
analyzing, by one or more processors, the data responsive to the selected patterns of data representing the selected signal characteristics and one or more predetermined patterns of the data of the one or more pipelines being displayed on the one or more displays, the one or more predetermined patterns of the data being indicators of potential stress corrosion cracking associated with the one or more pipelines, the analyzing comprising comparing the target pattern to the one or more selected patterns to identify a selected pattern of the one or more selected patterns that is consistent with the target pattern; and
determining, by one or more processors, one or more locations of potential stress corrosion cracking associated with the one or more pipelines responsive to the one or more of the predetermined patterns of data being displayed on the one or more displays, the determining comprising determining a location of the selected pattern of the one or more selected patterns that is consistent with the target pattern;
generating an excavation validation report identifying the one or more locations of potential stress corrosion cracking associated with the one or more pipelines, the excavation validation report identifying the location of the selected pattern of the one or more selected patterns that is consistent with the target pattern;
generating a request for a site excavation for at least one of the locations of one or more potential stress corrosion cracking associated with the one or more pipelines, the request for a site excavation requesting a site excavation at the location of the selected pattern of the one or more selected patterns that is consistent with the target pattern; and
conducting, responsive to the request, one or more site excavations to evaluate at least one of the locations of one or more potential stress corrosion cracking associated with the one or more pipelines, the one or more site excavations comprising a site excavation at the location of the selected pattern of the one or more selected patterns that is consistent with the target pattern.

44. A computer implemented method as defined in claim 43, wherein the determining the location of potential stress corrosion cracking includes identifying the presence of one or more patterns of the data that is consistent with the one or more predetermined patterns to identify the location of potential stress corrosion cracking in the one or more pipelines.

45. A computer implemented method as defined in claim 43, wherein the presence of the one or more patterns of the data that is consistent with the one or more predetermined patterns is identifiable responsive to one or more optimal display settings, the one or more patterns of the data that is consistent with the one or more predetermined patterns being representative of unique signal characteristics and being different than adjacent patterns representing adjacent signal characteristics being displaying on the one or more displays.

46. A computer implemented method as defined in claim 45, wherein the one or more displays are one or more color displays, and wherein the one or more predetermined patterns being displayed are displayed as one or more colors representing selected signal characteristics that are different than adjacent colors being displayed in the selected patterns, the adjacent colors representing adjacent signal characteristics on the one or more color displays.

47. A computer implemented method as defined in claim 43, wherein the analyzing includes applying one or more pipeline variable characteristics to the data being displayed on the one or more displays.

48. A computer implemented method as defined in claim 43, wherein each of the one or more site excavations comprises a physical excavation and visual inspection of the one or more pipelines at the location of the site excavation.

49. A computer implemented method as defined in claim 48, further comprising storing report data to generate the excavation validation report, updating the report data with confirmation data including whether confirmation of the presence of stress corrosion cracking at the excavated site occurred thereby to further assess additional data associated with the one or more pipelines, and wherein the additional data includes circumferential scan (C-scan) data of the one or more pipelines.

50. A computer implemented method as defined in claim 43, wherein the analyzing includes grading the selected patterns displayed on the one or more displays into one or more grade levels, the one or more grade levels including a first grade level (Grade A) defined as including all or most of a set of attributes of the one or more of the predetermined patterns and representing portions of the one or more pipelines with a high potential of being associated with stress corrosion cracking.

51. A computer implemented method as defined in claim 50, wherein the one or more grade levels includes the first grade level (Grade A), a second grade level (Grade B) defined as including some of the attributes of the one or more of the predetermined patterns and representing portions of the one or more pipelines to be considered for further assessment based on results from any investigations associated with the first grade level (Grade A), and a third grade level (Grade C) defined as having only passing resemblance to the one or more of the predetermined patterns and representing portions of the one or more pipelines to be considered for further evaluation if the portions of the one or more pipelines were to be exposed and inspected for other reasons in the future.

52. A computer implemented method as defined in claim 51, wherein the potential stress corrosion cracking has a location associated with the one or more predetermined patterns of data when displayed on the one or more displays comprising a non-erratic pattern being distinguished from other patterns on the one or more displays when a gain of the one or more selected patterns being displayed on the one or more displays is increased.

53. A computer implemented method as defined in claim 52, wherein the analyzing step further comprises determining optimal display settings, and wherein the determining the optimal display settings comprises changing a gain and offset of the one or more patterns of the magnetic flux leakage data being displayed on the one or more displays in order to achieve a high contrast display so that the presence of the one or more predetermined patterns is perceptible on the one or more displays.

54. A computer implemented method as defined in claim 53, wherein determining the optimal display settings on the one or more displays further comprises:
changing a longitudinal length along the one or more pipelines that the selected patterns of data being displayed on the one or more displays represents; and
changing a circumferential length about the one or more pipelines that the selected patterns of data displayed on the one or more displays represents.

55. A computer implemented method as defined in claim 43, wherein the excavation validation report comprises a validation dig list containing one or more potential stress corrosion cracking locations, whereby the validation dig list is used to identify areas along the one or more pipelines which are to be visually inspected for defects.

56. A computer implemented method as defined in claim 43, wherein the one or more pipelines are formed of steel, and the one or more stress corrosion cracking locations are a function of one or more steel properties.

57. Non-transitory storage medium having one or more computer programs stored thereon and readable by one or more processors, the one or more computer programs including a set of instructions that, when executed by the one or more processors, causes the one or more processors to perform the operations of:
determining a target pattern comprising an axial linear portion and a helical linear portion oriented diagonal to the axial linear portion, the axial linear portion corresponding to corrosion extending in a longitudinal direction along a length of a cylindrical pipeline, and the helical linear portion corresponding to corrosion extending in a helical direction about the cylindrical pipeline;
receiving magnetic flux leakage data from one or more pipeline inspection survey tools, the magnetic flux leakage data being associated with one or more joints of one or more longitudinal pipelines defining a pipeline joint;
displaying the magnetic flux leakage data on one or more displays as one or more selected patterns of data representing selected signal characteristics of the pipeline joint;
analyzing the magnetic flux leakage data being displayed on one or more of the displays for comparison with one or more predetermined patterns of magnetic flux leakage data, the one or more predetermined patterns of the magnetic flux leakage data being indicators of potential stress corrosion cracking associated with the pipeline joint, the analyzing comprising comparing the target pattern to the one or more selected patterns to identify a selected pattern of the one or more selected patterns that is consistent with the target pattern; determining one or more locations of potential stress corrosion cracking associated with the pipeline joint responsive to the one or more predetermined patterns of magnetic flux leakage data being displayed on the one or more displays, the determining comprising determining a location of the selected pattern of the one or more selected patterns that is consistent with the target pattern;
generating an excavation validation report identifying the one or more locations of potential stress corrosion cracking associated with the pipeline joint, the excavation validation report identifying the location of the selected pattern of the one or more selected patterns that is consistent with the target pattern; and
generating a request for a site excavation for at least one of the locations of one or more potential stress corrosion cracking associated with the pipeline joint, the request for a site excavation requesting a site excavation at the location of the selected pattern of the one or more selected patterns that is consistent with the target pattern,
wherein, responsive to the request, one or more site excavations are conducted to evaluate at least one of the locations of one or more potential stress corrosion cracking associated with the pipeline joint, the one or more site excavations comprising a site excavation at the location of the selected pattern of the one or more selected patterns that is consistent with the target pattern.

58. Non-transitory storage medium having one or more computer programs stored thereon as defined in claim 57, wherein the determining the location of potential stress corrosion cracking includes identifying the presence of the one or more patterns of the magnetic flux leakage data that is consistent with the one or more predetermined patterns to identify the location of potential stress corrosion cracking in the pipeline joint.

59. Non-transitory storage medium having one or more computer programs stored thereon as defined in claim 58, wherein the presence of the one or more patterns of the magnetic flux leakage data that is consistent with the one or more predetermined patterns is identifiable responsive to one or more optimal display settings, the one or more patterns of the magnetic flux leakage data that is consistent with the one or more predetermined patterns being representative of unique signal characteristics and being different than adjacent patterns representing adjacent signal characteristics being displayed on the one or more displays.

60. Non-transitory storage medium having one or more computer programs stored thereon as defined in claim 59, wherein the one or more displays being one or more color displays, and wherein the one or more patterns being displayed as one or more different colors than adjacent signal characteristics on the one or more color displays.

61. Non-transitory storage medium having one or more computer programs stored thereon as defined in claim 60, wherein the analyzing includes applying one or more pipeline variable characteristics to the magnetic flux leakage data being displayed on the one or more displays.

62. Non-transitory storage medium having one or more computer programs stored thereon as defined in claim 61, wherein each of the one or more site excavations comprises a physical excavation and visual inspection of the pipeline joint at the location of the site excavation.

63. Non-transitory storage medium having one or more computer programs stored thereon as defined in claim 62, wherein the set of instructions further causes the one or more processors to perform the operations of storing report data to generate the excavation validation report, updating confirmation data including whether confirmation of the presence of stress corrosion cracking at the excavated site occurred thereby to further assess additional magnetic flux leakage data associated with the one or more longitudinal pipelines, and wherein the additional magnetic flux data includes circumferential scan (C-scan) data.

64. Non-transitory storage medium having one or more computer programs stored thereon as defined in claim 57, wherein the analyzing includes grading the selected patterns of magnetic flux leakage data displayed on the one or more displays into one or more grade levels, the one or more grade levels including a first grade level (Grade A) defined as including all or most of a set of attributes of the one or more of the predetermined patterns and representing a pipeline joint with a high potential of being associated with stress corrosion cracking.

65. Non-transitory storage medium having one or more computer programs stored thereon as defined in claim 64, wherein the one or more grade levels includes the first grade level (Grade A), a second grade level (Grade B) defined as including some of the attributes of the one or more of the predetermined patterns and representing a pipeline joint to be considered for further assessment based on results from any investigations associated with the first grade level (Grade A), and a third grade level (Grade C) defined as having only passing resemblance to the one or more of the predetermined patterns and representing a pipeline joint to be considered for further evaluation if the pipeline joint were to be exposed and inspected for other reasons in the future.

66. Non-transitory storage medium having one or more computer programs stored thereon as defined in claim 58, wherein the potential stress corrosion cracking has a location associated with the one or more predetermined patterns of data when displayed on the one or more displays comprising a non-erratic pattern being distinguished from other patterns on the one or more displays when a gain of the one or more selected patterns being displayed on the one or more displays is increased.

67. Non-transitory storage medium having one or more computer programs stored thereon as defined in claim 58, wherein the analyzing step further comprises determining optimal display settings, and wherein the determining the optimal display settings comprises changing a gain and offset of the one or more patterns of the magnetic flux leakage data being displayed on the one or more displays in order to achieve a high contrast display so that the presence of the one or more predetermined patterns is perceptible on the one or more displays.

68. Non-transitory storage medium having one or more computer programs stored thereon as defined in claim 67, wherein determining the optimal display settings on the display further comprises:
 changing a longitudinal length along the one or more pipelines that the selected patterns of data being displayed on the one or more displays represents; and
 changing a circumferential length about the one or more pipelines that the selected patterns of data displayed on the one or more displays represents.

69. Non-transitory storage medium having one or more computer programs stored thereon as defined in claim 57, wherein the excavation validation report comprises a validation dig list containing one or more potential stress corrosion cracking locations, whereby the list facilitates identification of areas along the one or more longitudinal pipelines which are to be visually inspected for defects.

70. Non-transitory storage medium having one or more computer programs stored thereon as defined in claim 57, wherein the pipeline joint is formed of steel, and wherein the one or more stress corrosion cracking locations is a function of one or more steel properties.

\* \* \* \* \*